US011217725B2

(12) United States Patent
Soler et al.

(10) Patent No.: US 11,217,725 B2
(45) Date of Patent: Jan. 4, 2022

(54) LIGHT EMITTING APPARATUS WITH MELANOPIC EMISSION SPECTRUM

(71) Applicant: Biological Innovation and Optimization Systems, LLC, Carlsbad, CA (US)

(72) Inventors: Robert Soler, San Marcos, CA (US); William Coulter, Carlsbad, CA (US)

(73) Assignee: Biological Innovation and Optimization Systems, LLC, Carlsbad, CA (US)

( * ) Notice: Subject to any disclaimer, the term of this patent is extended or adjusted under 35 U.S.C. 154(b) by 356 days.

(21) Appl. No.: 16/270,936

(22) Filed: Feb. 8, 2019

(65) Prior Publication Data

US 2019/0267356 A1    Aug. 29, 2019

Related U.S. Application Data

(60) Provisional application No. 62/635,038, filed on Feb. 26, 2018.

(51) Int. Cl.
*H01L 33/32*     (2010.01)
*H01L 25/075*    (2006.01)
(Continued)

(52) U.S. Cl.
CPC ............. *H01L 33/32* (2013.01); *A61M 21/00* (2013.01); *H01L 25/0753* (2013.01);
(Continued)

(58) Field of Classification Search
CPC ...... H01L 25/0753; H01L 33/504–505; H05B 33/0845; H05B 33/0857
See application file for complete search history.

(56) References Cited

U.S. PATENT DOCUMENTS 8,031,938 B2    10/2011  Edge
9,039,746 B2     5/2015  Ven et al.
(Continued)

FOREIGN PATENT DOCUMENTS

CN       103715342 B    4/2016
WO    2016096367 A1    6/2016
WO    2017131714 A1    8/2017

OTHER PUBLICATIONS

International Search Report dated Jun. 5, 2019 for PCT Patent Application No. PCT/US2019/019298.
(Continued)

*Primary Examiner* — Vincent Wall
(74) *Attorney, Agent, or Firm* — MLO, a professional corp.

(57) ABSTRACT

A light emitting diode (LED) with a melanopic emission spectrum can comprise a primary light source and a phosphor. The primary light source can comprise an emission spectrum comprising a first peak centered at a wavelength from 480 nm to 500 nm. The phosphor, when excited, can comprise an emission spectrum with a second peak centered at a wavelength from 640 nm to 750 nm, and the intensity of the first peak is greater than the intensity of the second peak. A light emitting apparatus can comprise a first LED with a traditional white light emission spectrum, and a second LED with a melanopic emission spectrum. The light emitted from the apparatus can comprise chromaticity coordinates, in the CIE 1931 color space diagram using the 196410° Supplementary Standard Observer, that are within a one-step MacAdam ellipse from the black body locus with chromaticity coordinate x from 0.34 to 0.45.

17 Claims, 17 Drawing Sheets

(51) Int. Cl.
   *H01L 33/50*   (2010.01)
   *A61M 21/00*   (2006.01)
   *H05B 45/20*   (2020.01)

(52) U.S. Cl.
   CPC ........... *H01L 33/502* (2013.01); *H05B 45/20* (2020.01); *A61M 2021/0044* (2013.01)

(56) References Cited

U.S. PATENT DOCUMENTS

| | | |
|---|---|---|
| 9,605,815 B2 | 3/2017 | Yamakawa |
| 2010/0063566 A1 | 3/2010 | Uchiumi et al. |
| 2010/0259190 A1* | 10/2010 | Aikala ................... A01G 7/045 315/294 |
| 2011/0309773 A1* | 12/2011 | Beers ................... H05B 33/086 315/312 |
| 2012/0161170 A1* | 6/2012 | Dubuc ................... A01G 7/045 257/89 |
| 2012/0218750 A1* | 8/2012 | Klase ..................... F21V 5/007 362/231 |
| 2016/0262222 A1 | 9/2016 | Frohnapfel et al. |
| 2016/0366745 A1 | 12/2016 | Hikmet et al. |
| 2017/0086274 A1 | 3/2017 | Soler et al. |
| 2017/0146226 A1* | 5/2017 | Storey ..................... F21V 29/56 |
| 2017/0348506 A1 | 12/2017 | Berman et al. |

OTHER PUBLICATIONS

Extended European Search Report dated Nov. 4, 2021 for European Patent Application No. 19758035.0.

* cited by examiner

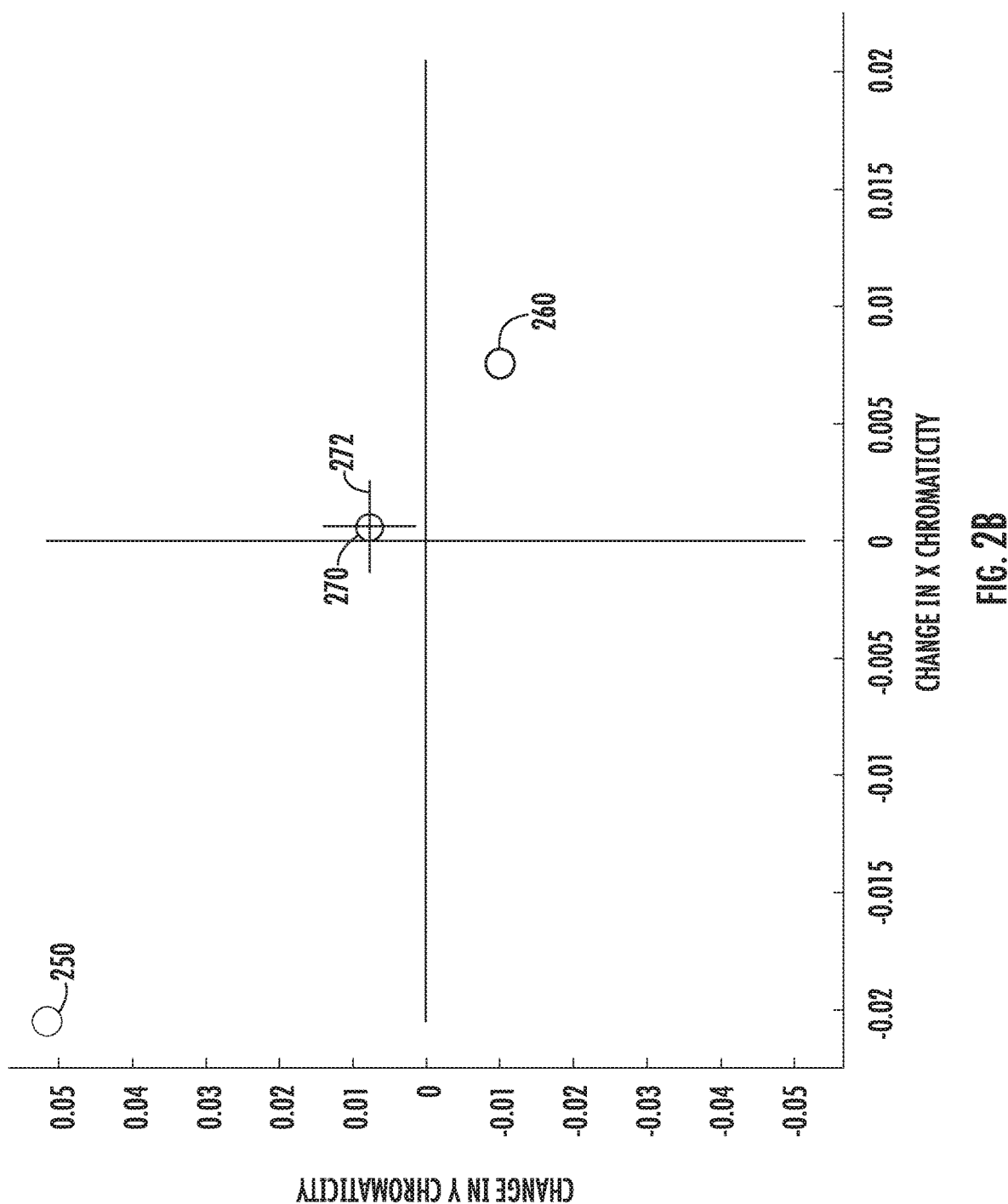

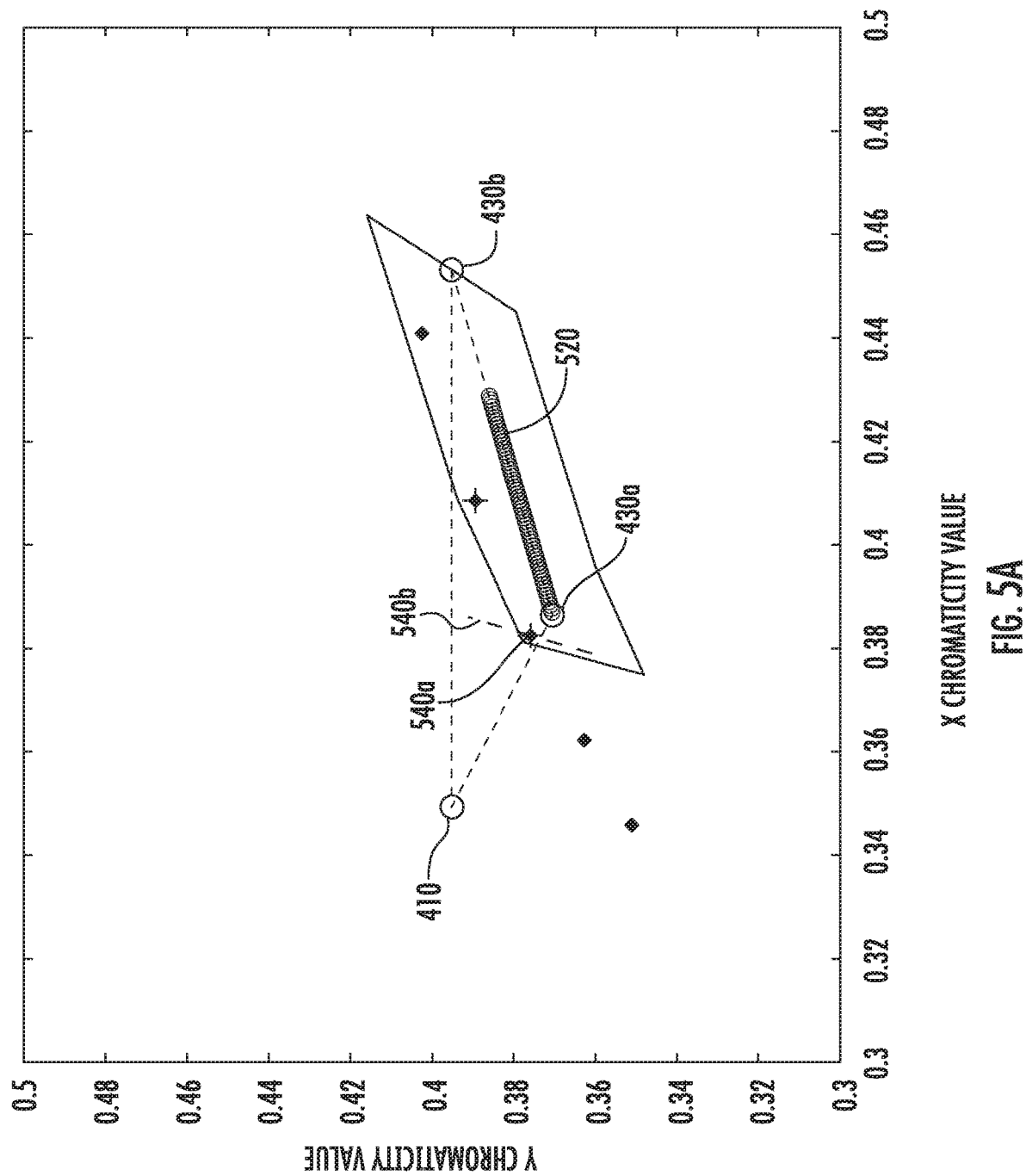

LIGHT EMITTING APPARATUS WITH MELANOPIC EMISSION SPECTRUM

RELATED APPLICATIONS

This application claims the benefit of U.S. Provisional Patent Application No. 62/635,038, filed on Feb. 26, 2018, and entitled "Systems and Methods of Human Centric Lighting"; which is hereby incorporated by reference for all purposes.

BACKGROUND

Circadian rhythms regulate a myriad of biological processes that culminate into higher level behaviors such as sleep and wake patterns. Light is the primary pathway by which circadian rhythms are regulated. A novel photoreceptor, containing a photopigment named melanopsin, directly projects to the suprachiasmatic nucleus, where the master clock is located. This points to an evolutionary relationship with the solar cycle. However, in modern society this relationship is broken, as we spend greater than 90% of our time indoors. This has led to a large variance of preferred sleep times, which in many cases are out of sync with social requirements.

Melanopsin photoreceptors are sensitive to a range of wavelengths and reach peak light absorption at wavelengths from approximately 480 nm to 500 nm. Recent scientific studies have shown that 480 nm to 500 nm light is an important stimulus for non-visual processes in humans, including physiological and neurological effects such as pupillary light reflex and circadian entrainment.

The human eye has three kinds of cone cells that sense light, having peaks of spectral sensitivity in short (e.g., 420 nm-440 nm), middle (e.g., 530 nm-540 nm), and long (e.g., 560 nm-580 nm) wavelengths. These cone cells are responsible for human color perception, and therefore three parameters corresponding to levels of stimulus of the three kinds of cone cells in principle describe any human color sensation. The International Commission on Illumination (CIE) 1931 color spaces were the first defined quantitative links between distributions of wavelengths in the electromagnetic visible spectrum, and physiologically perceived colors in human vision. The mathematical relationships that define these color spaces are essential tools for color management, and are important when dealing with color inks, illuminated displays, and recording devices such as digital cameras. The CIE 1931 RGB color space and CIE 1931 XYZ color space were created by the International Commission on Illumination in 1931. The tristimulus values associated with a color space (e.g., X, Y and Z in the CIE 1931 XYZ color space) can be conceptualized as amounts of three primary colors in a tri-chromatic, additive color model.

The three types of human vision sensors (cones) that are mimicked by the CIE color spaces, despite no drastic changes in visual perception, are not entirely uniform within the retina. The distribution of cone types is different throughout the retina. Not only is there is a strong presence of cones in the central field of view, known as the fovea, but the majority of the short wavelength cones reside outside of the foveal region. Additionally, the fovea and surrounding area are covered with a macular pigment, which attenuates short wavelengths of light. Traditionally, when mimicking perception of the foveal region (e.g., using CIE color spaces) the so-called 2-degree observer (referencing the narrow field of view observed by the foveal region) is used. Alternatively, the so-called 10-degree observer is used to mimic the perception of a wider field of view, which utilizes photoreceptors that are both within and outside the macular region.

Due to the distribution of cones and the macular pigment in the human eye, the tristimulus values of a color space depend on the observer's field of view. To eliminate this variable, the CIE defined a color-mapping function called the standard (colorimetric) observer, which represents the chromatic response within a 2-degree arc inside an average fovea. Correspondingly, the CIE 1931 Standard Observer function is also known as the CIE 19312-degree Standard Observer. A more modern but less-used alternative is the CIE 196410-degree Standard Observer, which represents the chromatic response between a 4 and 10-degree arc inside the extramacular region of an average retina.

SUMMARY

In some embodiments, a light emitting diode (LED) with a melanopic emission spectrum comprises a primary light source and a phosphor. In some embodiments, the primary light source has an emission spectrum comprising a first peak centered at a wavelength from 480 nm to 500 nm, the phosphor has an emission spectrum, when excited by the light from the primary light source, comprising a second peak centered at a wavelength from 640 nm to 750 nm, the intensity of the first peak is greater than the intensity of the second peak, and the light emitted from the LED comprises light emitted from the primary light source and the phosphor.

In some embodiments, a light emitting apparatus, comprises a first light emitting diode (LED) with an emission spectrum comprising a traditional white light emission spectrum, and a second LED with a melanopic emission spectrum. In some embodiments, the melanopic emission spectrum comprises a first peak centered at a wavelength from 480 nm to 500 nm, a second peak centered at a wavelength from 640 nm to 750 nm, wherein the intensity of the first peak is greater than the intensity of the second peak. In some embodiments, light is emitted from the light emitting apparatus comprising light from the first and second LEDs, and the emitted light comprises chromaticity coordinates (x,y), in the CIE 1931 color space diagram using the 196410° Supplementary Standard Observer, that are within a one-step MacAdam ellipse from the black body locus in the range of chromaticity coordinate x from 0.34 to 0.45.

BRIEF DESCRIPTION OF THE DRAWINGS

FIG. 2B shows the changes in chromaticity coordinates moving from the 2-degree observer to the 10-degree observer for the melanopic emission spectrum in FIG. 2A, the example traditional white LED spectrum, and the combined spectrum, in accordance with some embodiments.

FIG. 5A shows a section of the 1931 CIE color space diagram with an example supplemental LED and an example set of white LEDs, in accordance with some embodiments.

DETAILED DESCRIPTION

The present disclosure describes light emitting diodes (LEDs) with melanopic emission spectra that have improved visual aesthetic qualities compared to conventional circadian LED systems. In some embodiments, the chromaticity coordinates of the LEDs with melanopic emission spectra are tailored according to various criteria (e.g., within a CIE color space), optionally with a particular observer (e.g., 2-degree or 10-degree). In some embodiments, light from an LED with a melanopic emission spectrum is combined with light from a white LED, and the combined light has a color that appears white to a typical observer. The term "melanopic light" or "melanopic emission spectrum" as used herein refers to light or an emission spectrum that includes a strong intensity peak in the wavelength range from 480 nm to 500 nm.

In some embodiments, the spectrum of light from a light emitting apparatus is engineered (or tailored) to have desired chromaticity coordinates (e.g., in the CIE 1931 color space diagram using the 1964 10° Supplementary Standard Observer). For example, an LED can have an emission spectra with a strong peak in the range of 480 nm to 500 nm and the spectrum of the LED can be tailored such that when the LED is combined with a traditional white LED (e.g., with a spectrum shown in FIG. 1A) the combined light appears white (e.g., has chromaticity coordinates within the ANSI 4000 K Bin in the CIE 1931 color space diagram).

Figure 1A:
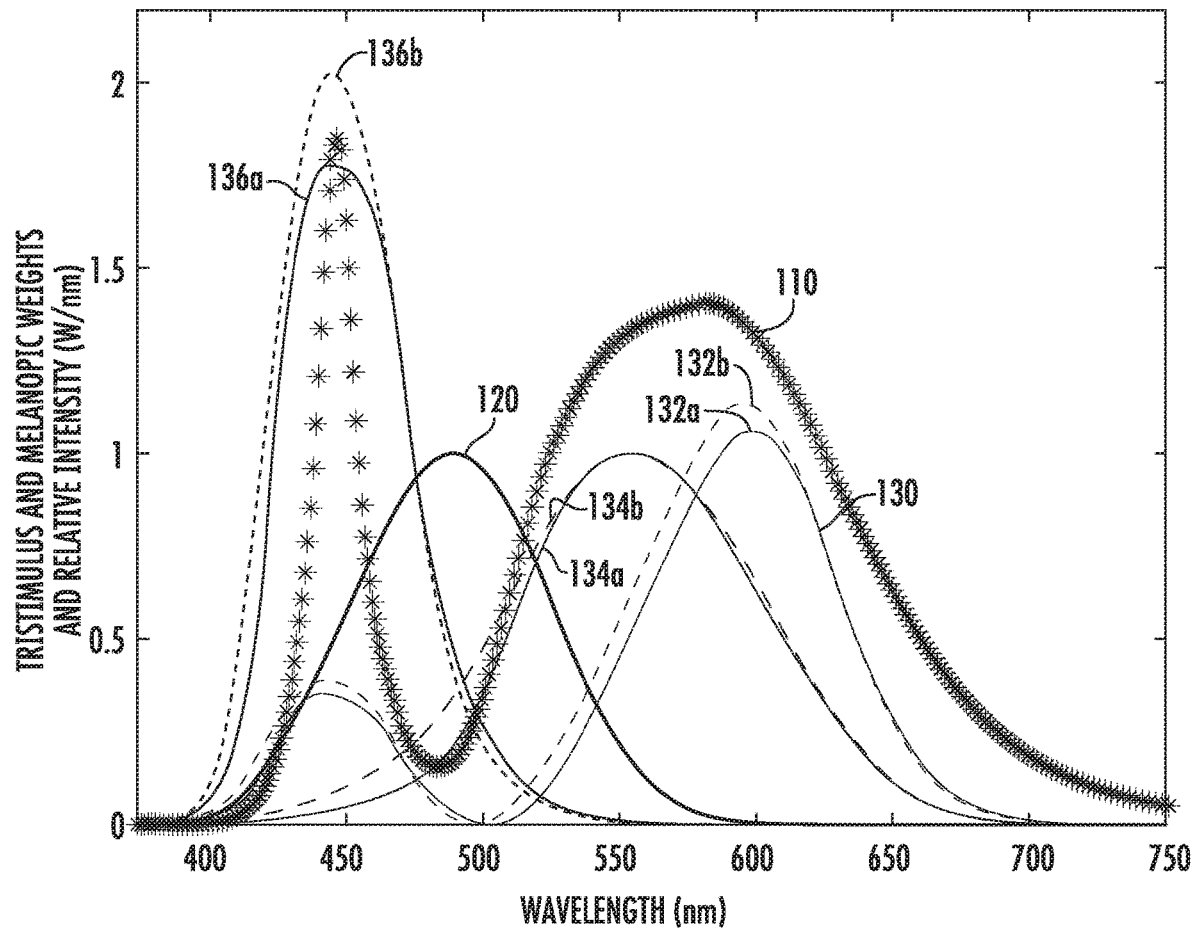
FIG. 1A (Prior Art) shows an example of a typical LED with a traditional white light emission spectrum, the melanopic efficiency curve, and an example of 6 curves for the three color-matching functions (one for each tristimulus value) in both the 2-degree observer and the 10-degree observer for the traditional white LED spectrum.

The circadian rhythms that regulate a myriad of biological processes and are chiefly regulated by light are broken in modern society since people spend a large fraction of their time indoors. This problem is exacerbated by the fact that LED lighting has very little energy in the peak sensitivity of melanopsin. Melanopsin photoreceptors, which are critical for non-visual stimuli including physiological and neurological effects, such as pupillary light reflex and circadian entrainment, have peak light absorption at wavelengths from approximately 480 nm to 500 nm. FIG. 1A shows an example of a typical LED with a traditional white light emission spectrum 110, where the y-axis units are Relative Intensity (W/nm), containing a stronger sharp (primary) peak at approximately 450 nm and a weaker broader (secondary) peak from approximately 520 nm to 640 nm. The figure also shows the "melanopic efficiency curve" 120, which is a normalized weighted responsivity spectrum of the melanopsin photoreceptors. The figure shows that traditional white LED spectra typically has little intensity in the range where melanopsin photoreceptors are strongly responsive.

Psychophysics color matching functions have been created for both the CIE 1931 2-degree Standard Observer (i.e. the 2-degree observer) and the CIE 1964 10-degree Standard Observer (i.e., the 10-degree observer) in the 1931 CIE color space. Conventional industry norms, such as for communicating the color of light and for color measurement devices, rely on the 2-degree observer, and in many situations, the 2-degree observer is adequate to describe a perceived color relatively accurately. Surprisingly, this is not the case for many spectra that include a melanopic emission spectrum and seek to appear white. In many cases, the present embodiments uniquely recognize that for a spectrum from a light emitting apparatus that includes at least one light source with a melanopic emission spectrum, the 10-degree observer can describe the perceived color of the spectrum more accurately than the 2-degree observer.

Conventionally, LEDs are color-matched (e.g., to a white light standard, or a 4000 K white light) using the 2-degree observer in the CIE 1931 color space diagram. Surprisingly, the present methods utilize a unique discovery that this convention is inadequate when color-matching LEDs with significant amounts of melanopic light, and leads to illumination spectra that appear mis-matched to an average observer (i.e., an average human). For color-matching LEDs with significant amounts of melanopic light, the present methods use the 10-degree observer in the CIE 1931 color space diagram yield the superior color-matching result of spectra that appear matched to an average observer.

For example, in a study performed in relation to this disclosure, conventional methods using the 2-degree observer and present methods using the 10-degree observer were compared to tune the intensity ratio of light from a set of LEDs. The intensity ratio of the set of tuned LEDs was tuned such that the combined light had chromaticity coordinates within a region of the CIE 1931 color space diagram that was white (e.g., within the 4000 K ANSI Bin) using both the 2-degree and the 10-degree observers. The first LED of the set of tuned LEDs had a significant amount melanopic light and the second LED of the set of tuned LEDs was a traditional white LED. U.S. Pat. Nos. 9,844,116 and 9,788,387 describe systems and methods for controlling the spectral content of LED lighting devices by combining multiple LEDs with different colors (i.e., with different emission spectra), and further explain how the LED intensity ratio was tuned such that the combined light had certain chromaticity coordinates. The tuned LED combination was used to illuminate one white box, and a traditional LED with the same correlated color temperature (CCT) as the tuned LEDs was used to illuminate a second white box. The two white boxes were placed side-by-side and observers were given questionnaires in order to assess their perceptions of the different colors.

The results of the above study were as follows. The average observer determined that the color of the combined light from the 2 tuned LEDs whose intensity ratio was tuned using the 2-degree observer did not match the color of the traditional LED with the same CCT as the 2 tuned LEDs. The average observer also determined that the color of the combined light from the 2 tuned LEDs whose intensity ratio was tuned using the 2-degree observer appeared less white than the color of the traditional white LED. Surprisingly, the results were different when the 10-degree observer was used. The average observer determined that the color of the combined light from the 2 tuned LEDs whose intensity ratio was tuned using the 10-degree observer did match the color of the traditional LED with the same CCT as the 2 tuned LEDs. In other words, these results show that when the 2-degree observer was used, despite the fact that the resulting calibrated spectrum should have been visibly the same according to all measurement equipment, the perceived color was in fact different. Furthermore, it was determined that the 10-degree observer color matching functions were better predictors of the actual perceived color of an individual. The average observer also determined that the color of the combined light from the 2 tuned LEDs whose intensity ratio was tuned using the 10-degree observer appeared approximately as white as the color of the traditional white LED.

In the present embodiments, therefore, the 10-degree observer is used to tailor the chromaticity coordinates of light from a set of LEDs such that the combined light from the LEDs appears white to a typical observer. Several examples, and further explanations are described in more detail below.

In some cases, when the 2-degree observer is used, the combined light from the tuned LEDs above also appears slightly greenish, which is commonly considered an undesirable color of light for a white light source intended for lighting applications. However, when the 10-degree observer is used, the combined light from the tuned LEDs above appears approximately the same color as the white LED.

One way to describe the difference in chromaticity coordinates of a particular light source determined using the 2-degree observer and the 10-degree observer is through vector shifts in the coordinates in the CIE 1931 color space diagram. LEDs with large vector shifts are more sensitive to the observer (i.e., the perceived color will be more likely to be perceived as different when color-matched using different observers), while LEDs with smaller shifts are less sensitive to the observer.

In some embodiments, LEDs with melanopic emission spectra are designed to have vector shifts in their chromaticity coordinates from the 2-degree observer to the 10-degree observer in the CIE 1931 color space diagram, in the negative X and positive Y directions. This is in contrast with traditional white light LEDs which have vector shifts when moving from the 2-degree to the 10-degree observers in the positive X and negative Y directions. In some embodiments, the large shift in the chromaticity coordinates between the 2-degree to the 10-degree observers for LEDs with melanopic emission spectra requires that the 10-degree observer is used when tailoring the chromaticity coordinates of these LEDs.

Figure 1B:
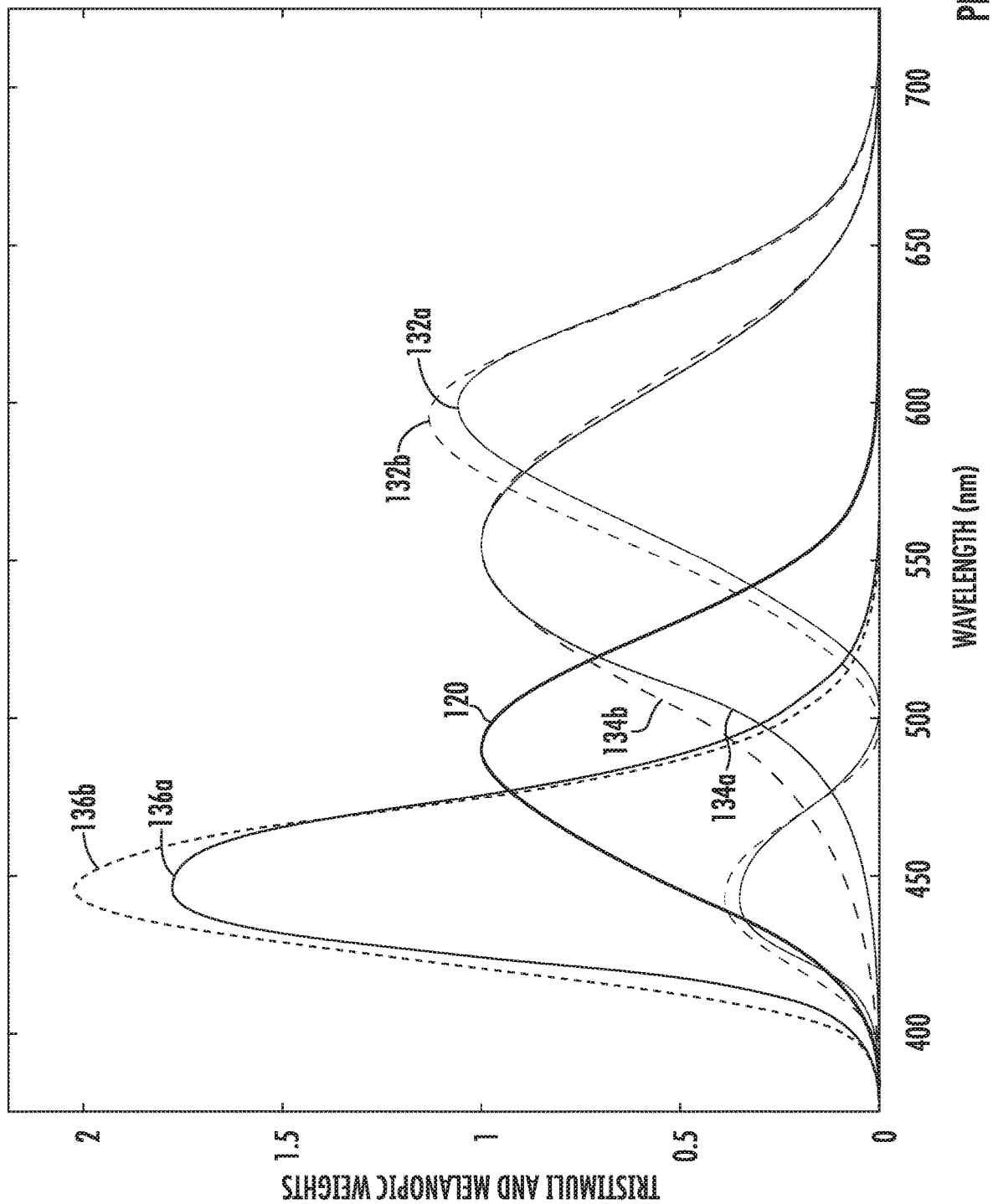
FIG. 1B (Prior Art) shows the melanopic efficiency curve, and an example of 6 curves for the three color-matching functions (one for each tristimulus value) in both the 2-degree observer and the 10-degree observer for the traditional white LED spectrum in FIG. 1A.

FIG. 1A also shows 6 curves for the three color-matching functions 130 ("CMF," one for each tristimulus value) in both the 2-degree observer (solid lines) and the 10-degree observer (dashed lines) for the traditional white LED spectrum 110. Each of these color-matching functions are labeled in FIG. 1B, where 132a, 134a and 136a are the X, Y and Z color matching functions, respectively, in the 2-degree observer, and 132b, 134b and 136b are the X, Y and Z color matching functions, respectively, in the 10-degree observer. In FIG. 1B, the melanopic efficiency curve 120 is again included for reference. The differences between the 2-degree and 10-degree color matching functions for a traditional white LED are illustrated by the differences between the pairs of curves in FIG. 1B. The figure shows that the largest discrepancy between the two models lie in the regions near 450 nm (between curves 136a and 136b) and 490 nm (between curves 134a and 134b). These differences are particularly important for LED lighting, as traditional LED lighting has a peak emission in the 450 nm range and a trough in the 490 nm range (e.g., as shown in the example spectrum 110 in FIG. 1A). The 450 nm peak and 490 nm trough in traditional LED lighting spectra have also led to the aforementioned exacerbation of the circadian dysfunction.

Figure 2A:
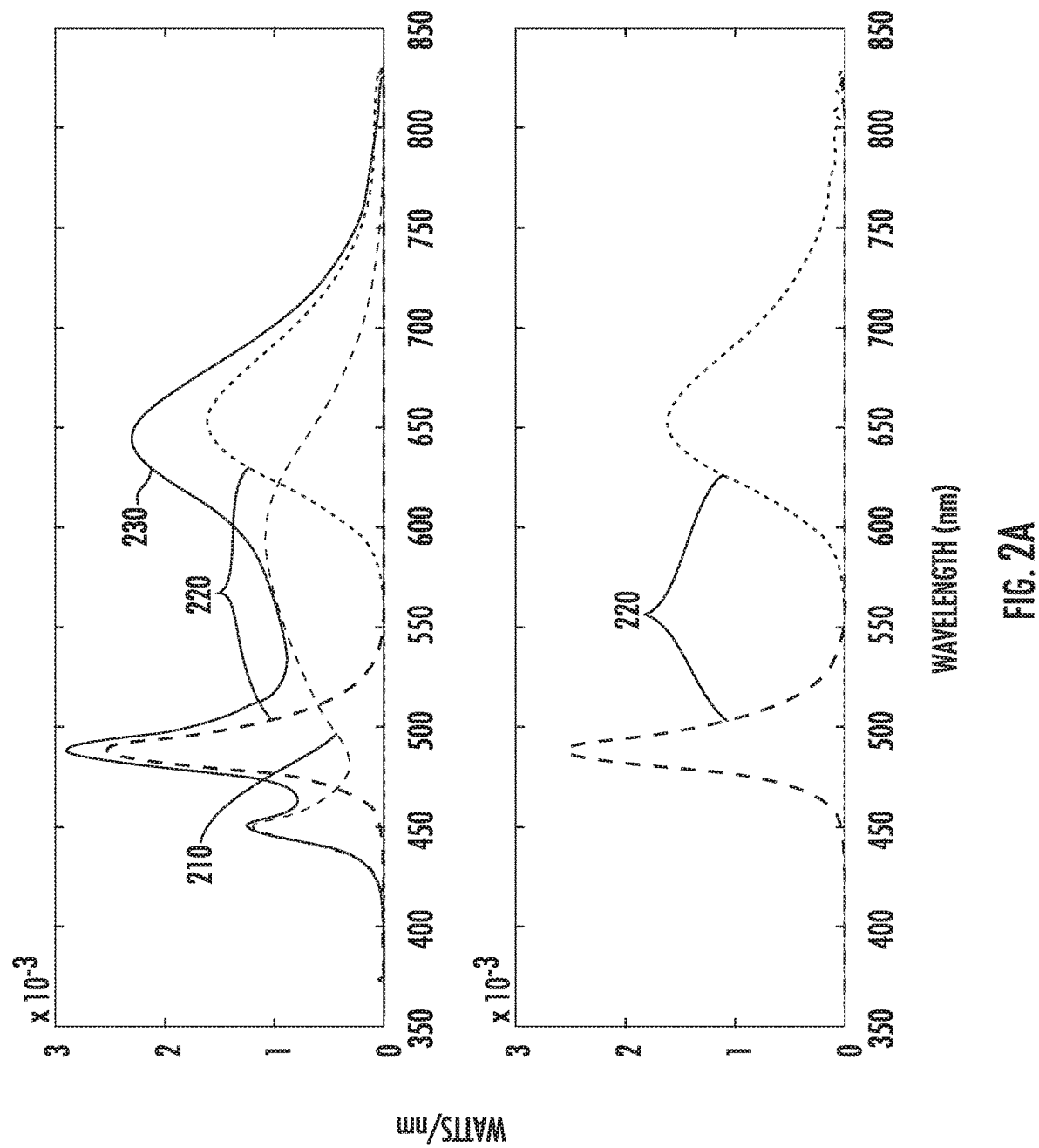
FIG. 2A shows an example of a spectrum for a supplemental LED with emphasis in the melanopic region, and the combined spectrum created when such an LED is combined with a traditional white light LED spectrum, in accordance with some embodiments.

In some embodiments, light from a white light LED is combined with light from an LED having a melanopic emission spectrum and the combined light appears white to an average observer. The white light LED can be any LED that has an emission spectrum whose chromaticity coordinates are close to the black body locus (in either the 2-degree or 10-degree observer). FIG. 2A shows an example of a spectrum for a supplemental LED 220 with emphasis in the melanopic region, and the combined spectrum 230 created when such an LED is combined with a traditional white light LED spectrum 210. Spectrum 210 is an example spectrum from a 3500 K white light LED.

In some embodiments, the spectrum from an LED with a melanopic emission spectrum, and/or the spectrum created from combining the light from an LED with a melanopic emission spectrum (e.g., supplemental LED 220) and the light from a white light LED (e.g., a traditional white light LED), has one or more of the following properties. In some embodiments, the total radiant power in a second wavelength band from 500 nm to 700 nm is greater than half of the total radiant power in the spectrum. In some embodiments, the maximum power density in a wavelength band from 480 nm to 500 nm is greater than the maximum power density in a wavelength band from 400 nm to 480 nm. In some embodiments, the spectral intensity profile has a peak in a wavelength band from 480 nm to 500 nm, the power density of the peak being greater than the maximum power density in a wavelength band from 400 nm to 480 nm. In some embodiments, the total radiant power in a wavelength range from 400 nm to 450 nm is less than 10% of the total radiant power in the spectrum. In some embodiments, the total radiant power in the wavelength range from 450 nm to 500 nm is greater than 15% (or greater than 10%, or greater than 20%) of the total radiant power in the spectrum. In some embodiments, the total radiant power in the wavelength range from 400 nm to 440 nm is less than 5% (or less than 10%) of the total radiant power in the spectrum. In some embodiments, the maximum power density in the wavelength range from 480 nm to 500 nm is at least 1.8 times greater than the maximum power density in the wavelength range from 400 nm to 480 nm. In some embodiments, the maximum power density in the wavelength range from 480 nm to 500 nm is at least 80% (or at least 70%, or at least 90%) of the maximum power density in the wavelength range from 500 nm to 700 nm. In some embodiments, the total radiant power in a first wavelength band from 460 nm to 500 nm is greater than total radiant power in a second wavelength band from 500 nm to 700 nm. In some embodiments, the total radiant power in a wavelength band from 400 nm to 440 nm is less than 4% (or less than 2%, or less than 5%, or less than 10%) of the total radiant power in the spectrum. In some embodiments, the maximum power density in the wavelength range from 470 nm to 500 nm is at least 1.5 times greater than the maximum power density in the wavelength range from 400 nm to 470 nm. In some embodiments, the maximum power density in the wavelength range from 480 nm to 500 nm is at least 80% of the maximum power density in the wavelength range from 500 nm to 700 nm. In some embodiments, the maximum power density in the wavelength range from 480 nm to 500 nm is at least 1.8 times greater than the maximum power density in the wavelength range from 400 nm to 480 nm. In some embodiments, the power density at 660 nm is at least 75% (or at least 70%, or at least 80%) of the power density at 630 nm.

Additionally, in some embodiments, the present LEDs with melanopic emission spectra also utilize biological light that includes multiple wavelengths having biological significance. The suprachiasmatic nuclei in the hypothalamus regulate circadian rhythms using input from ganglion cells in the retina. The ganglion cells contain proteins called opsins, where melanopsin (Opn4) responds to the wavelength of 490 nm. Illumination profiles of the present LEDs with melanopic emission spectra include this melanopsin spectral component relevant to optical input. Illumination profiles of the present LEDs with melanopic emission spectra can also include enhanced spectral components that are relevant to the skin's optical window and sub-dermal cellular stimulation (e.g., deep-red around 660 nm and/or infrared). Some embodiments uniquely utilize LEDs with spectra that include both 490 nm for optical stimulation and 660 nm for sub-dermal cellular stimulation. Furthermore, in a recent study by Ota, et al., "Impaired Circadian Photoentrainment in Opn4-Null Mice," iScience, p. 299-305, Aug. 31, 2018, it was found that Opn5, which has peak absorption at 380 nm, also plays a role in photoentrainment. In some embodiments, the lighting spectra of present LEDs with melanopic emission spectra may also uniquely include a peak wavelength at around 380 nm.

FIG. 2B shows the changes in chromaticity coordinates moving from the 2-degree observer to the 10-degree observer 250, 260 and 270 for the melanopic emission spectrum 220, the example traditional white LED spectrum 110, and the combined spectrum 230, respectively. FIG. 2B also shows the changes in chromaticity coordinates moving from the 2-degree observer to the 10-degree observer 272 for a combined spectrum from a melanopic emission spectrum 220, and a traditional white LED spectrum with a CCT of 3500 K. The change in the x or y chromaticity coordinate is defined herein as the x or y chromaticity coordinate in the 2-degree observer subtracted from the x or y chromaticity coordinate in the 10-degree observer. FIG. 2B shows that the emitted light from the example LED supplement will have a substantially different vector shift 250 compared to the vector shift 260 of the traditional LED. In some embodiments, the vector shift of an LED supplement with a melanopic emission spectrum is not only in the opposite direction as the shift for traditional white LEDs, but it has a magnitude greater than four times that of a shift for a traditional LED. Additionally, in some embodiments, the combined light of a supplemental LED and traditional white light LED (e.g., having spectrum 230 in FIG. 2A) will have a significantly different vector shift from the 2-degree to the 10-degree observer compared with either of the constituent LEDs. For example, the combined spectrum 230 has a vector shift 270 with a small magnitude, and in a completely different quadrant from either of the constituent LEDs.

In some embodiments, the light emitting apparatus contains a supplemental LED and a white LED, and the light from the two LEDs combine to produce white light emitted from the apparatus that appears white to an average person. In some embodiments, a supplemental LED has a shift in the chromaticity coordinates (x,y) from the chromaticity coordinates using the 1931 2° Standard Observer to the chromaticity coordinates using the 1964 10° Supplementary Standard Observer, in the CIE 1931 color space diagram, from −0.025 to −0.01 in the x-coordinate, and from 0.04 to 0.09 in the y-coordinate. In some embodiments, has a shift in the chromaticity coordinates (x,y) with a magnitude greater than 0.04, or greater than 0.05, or greater than 0.06, or greater than 0.07, or from 0.04 to 0.10.

A supplemental LED with emphasis in the melanopic region (e.g., an LED with spectrum 220 in FIG. 2A) can be added to any white LED (e.g., an LED with the traditional white light LED spectrum 210) and the combined spectrum can appear white. In some embodiments, the combined light from the two LEDs has a spectrum with a global maximum from 480 nm to 500 nm. In some embodiments, the combined light from the two LEDs has a color rendering index (CRI) greater than 70, or greater than 75, or greater than 80, or greater than 85. In some embodiments, the combined light from the two LEDs has a cyanosis observation index (COI) less than 3.1, or less than 3.3, or less than 3.5. In some embodiments, the combined light from the two LEDs is strongly absorbed by melanopsin and satisfies proper circadian regulation in humans.

In some embodiments, the supplemental LED has a first peak centered at a wavelength from 480 nm to 500 nm, or from 490 nm to 500 nm, or from 480 nm to 490 nm, or at approximately 490 nm. In some embodiments, the supplemental LED a second peak centered at a wavelength from 640 nm to 750 nm, or from 740 nm to 800 nm, or at approximately 640 nm, or at approximately 680 nm, or at approximately 720 nm, or at approximately 740 nm, or at approximately 780 nm, or greater than 640 nm. In some embodiments, the ratio of maximum intensity of the first peak to the maximum intensity of the second peak is greater than 1, or greater than 2, or greater than 3, or is from 1 to 5. In some embodiments, the supplemental LED has chromaticity coordinates in the CIE 1931 color space diagram using the 1964 10° Supplementary Standard Observer, comprise x from 0.22 to 0.43, and y from 0.34 to 0.47.

In some embodiments, the supplemental LED (e.g., an LED with a melanopic emission spectrum) contains a primary light source and a phosphor. An example of a primary light source is an LED with InGaN light emitting materials (e.g., a doped InGaN LED with an emission peak at about 490 nm), although any LED light source with the appropriate emission spectrum can be used. Some examples of phosphor materials are $CaAlSiN_3:Eu_2$+(CASN phosphor), and $Sr[LiAl_3N_4]:Eu^{2+}$, however, any phosphor material with the appropriate emission spectrum can be used. For example, the primary light source can emit light that makes up the first peak (e.g., centered at a wavelength from 480 nm to 500 nm), and the phosphor can emit light that makes up the second peak (e.g., centered at a wavelength from 640 nm to 660 nm, or from 640 nm to 750 nm). In some embodiments, the spectrum from such a supplemental LED will have a first peak from the primary light source, and a second peak emitted by the phosphor, and the intensity of the first peak is greater than the intensity of the second peak, or intensity of the first peak is 1.5 times, or 2 times, or 3 times, or 5 times, or more than 2 times greater than the intensity of the second peak. A supplemental LED with a melanopic emission spectrum can benefit from the inclusion of a phosphor because it can simplify a lighting system incorporating the LED. For example, when a supplemental LED with a single peak in the melanopic emission spectral range (e.g., from 480 nm to 500 nm) is combined with an LED with a traditional white light emission spectrum in a system, the combined light can appear greenish and a third light source can be required to tune the combined light to appear white. In some embodiments, the third light source is a third LED (e.g., with a single emission peak in the 640 nm to 750 nm range), which will increase the complexity of the system. In other embodiments, the supplemental LED can include a phosphor (e.g., with an emission peak in the 640 nm to 750 nm range) and the phosphor will serve as the third light source. In that case, there are only two LEDs (i.e., 2-channel systems) in the system to control, rather than three (i.e., three-channel systems), which is beneficial because it simplifies the system. In some cases, there are also advantages to using controllable additional light sources, rather than a supplemental LED with a phosphor, such as improved tunability of the system in operation. This is because the ratio of the emission intensity of the phosphor and the primary light source in the supplemental LED is fixed, in contrast with systems that include multiple LEDs with a control system capable of changing the amount of emission from each LED during operation.

In some embodiments, the supplemental LED comprises a primary light source and a phosphor, and the chromaticity coordinates (x,y) of the emission spectrum from the primary light source, in the CIE 1931 color space diagram using the 1964 10° Supplementary Standard Observer, comprise x from 0.06 to 0.1, and y from 0.36 to 0.53. In some embodiments, the supplemental LED comprises a primary light source and a phosphor, and the chromaticity coordinates (x,y) of the emission spectrum from the phosphor, in the CIE 1931 color space diagram using the 1964 10° Supplementary Standard Observer, comprise x from 0.55 to 0.68, and y from 0.31 to 0.4, or x from 0.66 to 0.68, and y from 0.31 to 0.33. In some embodiments, the spectrum emitted from such a supplemental LED will have chromaticity coordinates (x,y), in the CIE 1931 color space diagram using the 1964 10° Supplementary Standard Observer, x from 0.22 to 0.43, and y from 0.34 to 0.47. In some embodiments, the spectrum emitted from such a supplemental LED will have chromaticity coordinates (x,y), in the CIE 1931 color space diagram, that shift in the negative x direction and the positive y direction from the chromaticity coordinates using the 1931 2° Standard Observer to the chromaticity coordinates using the 1964 10° Supplementary Standard Observer. In some embodiments, the spectrum emitted from such a supplemental LED will have a shift between the chromaticity coordinates using the 1931 2° Standard Observer and the chromaticity coordinates using the 1964 10° Supplementary Standard Observer, in the CIE 1931 color space diagram, in the x-coordinate from −0.025 to −0.01, and a shift in the y-coordinate from 0.04 to 0.09. In some embodiments, the spectrum emitted from such a supplemental LED will have a shift between the chromaticity coordinates using the 1931 2° Standard Observer and the chromaticity coordinates using the 1964 10° Supplementary Standard Observer, in the CIE 1931 color space diagram, that has a magnitude greater than 0.04. In some embodiments, the spectrum emitted from such a supplemental LED will have chromaticity coordinates (x,y), in the CIE 1931 color space diagram, that are below the black body locus using the 1931 2° Standard Observer and above the black body locus using the 1964 10° Supplementary Standard Observer.

In some embodiments, the supplemental LED (e.g., an LED with a melanopic emission spectrum) contains a primary light source and two phosphors. In some such cases, the primary light source can be totally (or almost totally) absorbed by the two phosphors such that the light emitted from the LED contains light emitted from the two phosphors, and no light (or almost no light) from the primary light source. For example, the primary light source can emit high energy light (e.g., with a wavelength from 400 nm to 450 nm), the first phosphor can emit light that makes up a first peak in the emitted spectrum (e.g., centered at a wavelength from 480 nm to 500 nm), and the second phosphor can emit light that makes up a second peak in the spectrum (e.g., centered at a wavelength from 640 nm to 660 nm, or from 640 nm to 750 nm). In some embodiments, the spectrum emitted from such a supplemental LED will have chromaticity coordinates (x,y), in the CIE 1931 color space diagram using the 1964 10° Supplementary Standard Observer, x from 0.22 to 0.43, and y from 0.34 to 0.47. In some embodiments, the spectrum emitted from such a supplemental LED will have chromaticity coordinates (x,y), in the CIE 1931 color space diagram, that shift in the negative x direction and the positive y direction, or in the positive x direction and the positive y direction, from the chromaticity coordinates using the 1931 2° Standard Observer to the chromaticity coordinates using the 1964 10° Supplementary Standard Observer. In some embodiments, the spectrum emitted from such a supplemental LED will have a shift between the chromaticity coordinates using the 1931 2° Standard Observer and the chromaticity coordinates using the 1964 10° Supplementary Standard Observer, in the CIE 1931 color space diagram, in the x-coordinate from −0.025 to −0.01, and a shift in the y-coordinate from 0.04 to 0.09. In some embodiments, the spectrum emitted from such a supplemental LED will have a shift between the chromaticity coordinates using the 1931 2° Standard Observer and the chromaticity coordinates using the 1964 10° Supplementary Standard Observer, in the CIE 1931 color space diagram, that has a magnitude greater than 0.04. In some embodiments, the spectrum emitted from such a supplemental LED will have chromaticity coordinates (x,y), in the CIE 1931 color space diagram, that are below the black body locus using the 1931 2° Standard Observer and above the black body locus using the 1964 10° Supplementary Standard Observer.

In some embodiments, the white LED combined with the supplemental LED is a traditional white light LED, or is an LED with a 3000 K CCT, or with a 3500 K CCT, or with a 4000 K CCT, or with a CCT from 3000 K to 4000 K, or with chromaticity coordinates approximately within the ANSI 3000 K, ANSI 3500 K Bin, or ANSI 4000 K Bin, or with chromaticity coordinates approximately on the black body locus. Some additional non-limiting examples of white light LEDs that can be used with the present LEDs having melanopic emission spectra are LEDs with or without a phosphor, LEDs with multiple sub-LEDs that combine to produce white light (e.g., with a CCT of 3500 K or 4000 K), organic LEDs, and/or laser-based white light sources. In some embodiments, the white LED combined with the supplemental LED is a traditional white light LED, and the chromaticity coordinates (x,y) of the emission spectrum from the primary light source, in the CIE 1931 color space diagram using the 1964 10° Supplementary Standard Observer, comprise x from 0.36 to 0.59, and y from 0.36 to 0.44. In some embodiments, the white LED combined with the supplemental LED is a traditional white light LED, and the chromaticity coordinates (x,y) of the emission spectrum from the primary light source, in the CIE 1931 color space diagram using the 1964 10° Supplementary Standard Observer, comprise x from 0.39 to 0.5, and y from 0.37 to 0.43. In some embodiments, the white LED has chromaticity coordinates in the CIE 1931 color space diagram using the 1964 10° Supplementary Standard Observer, comprise x from 0.40 to 0.42, and y from 0.38 to 0.40.

Conventionally, adding an LED with a melanopic emission spectrum to a traditional white LED has an adverse visual effect on the combined light when color matched to a traditional LED, and the combined light is perceived as much greener than its color matched LED. Even a small amount of emission in the melanopic wavelength range (i.e., 480 nm to 500 nm) can cause such a problem. Unexpectedly, the cause of this problem is due to the shift between the commonly used 2-degree observer and the 10-degree observer for spectra containing significant light in the 480 nm to 500 nm range. Therefore, in some embodiments, a supplementary LED with a melanopic emission spectra including emitted wavelengths outside of the 480 nm to 500 nm range to adjust the visual spectra when combined with a traditional white LED is combined with a traditional white LED, and the combined light is perceived as white by tailoring the chromaticity coordinates of the LED with a melanopic emission spectra using the 10-degree observer.

Figure 2C:
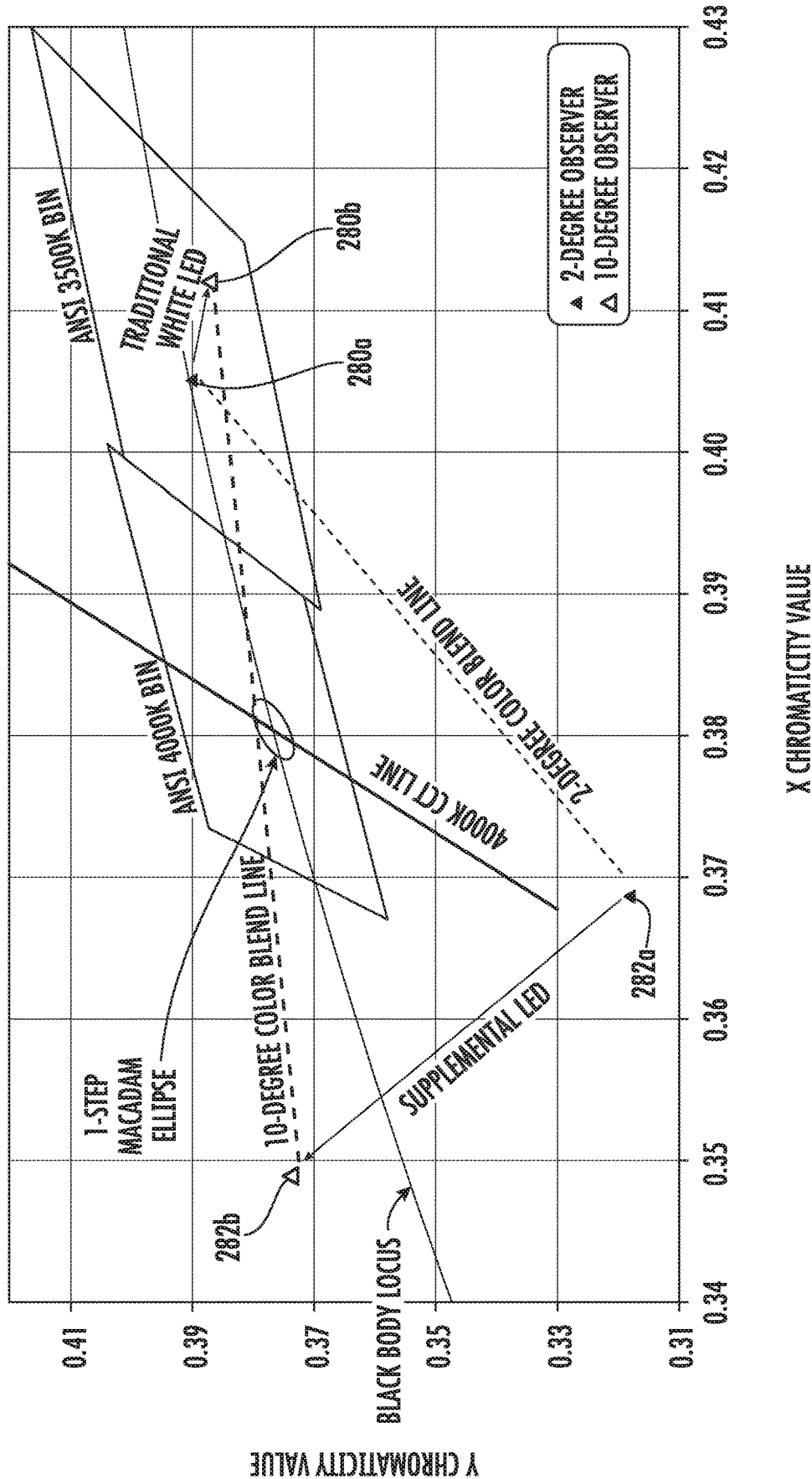
FIG. 2C shows an example of chromaticity coordinates for a traditional white LED in the 2-degree observer and the 10-degree observer, and the supplemental LED with spectrum 220 in FIG. 2A in the 2-degree observer and the 10-degree observer, in accordance with some embodiments.

FIG. 2C shows an example of chromaticity coordinates for a traditional white LED in the 2-degree observer (280a) and the 10-degree observer (280b), and the supplemental LED with spectrum 220 in FIG. 2A in the 2-degree observer (282a) and the 10-degree observer (282b). The light from the two LEDs (the traditional white light LED and the supplemental LED) can be combined in a light emitting apparatus to create a combined (i.e., mixed or blended) spectrum. The "2-degree color blend line" connects the 2-degree observer chromaticity coordinates for the two LEDs, and the "10-degree color blend line" connects the 10-degree observer chromaticity coordinates for the two LEDs. These color blend lines describe the possible chromaticity coordinates of the combined spectra from the two LEDs when mixed in different amounts. For example, the ratio of the light emission intensities of the two LEDs can be tuned by changing the relative amount of current used to drive the two LEDs. By changing the ratio of the emission intensities of the two LEDs, the color of the combined light can be tuned. In some embodiments, the emission intensity of the supplemental LED is greater than that of the traditional white light LED. In some embodiments, the ratio of the emission intensities of the two LEDs is tuned such that the combined light appears white, and has a sufficient amount of melanopic light (e.g., the ratio of melanopic lux to total photopic lux in the combined light greater than 0.7). In some embodiments, the ratio of the emission intensities of the two LEDs is tuned such that the combined light contains more melanopic light than the traditional white LED. In some embodiments, the ratio of the emission intensities of the two LEDs is tuned such that the combined light contains more melanopic light than a traditional white LED with a CCT that is 2 or 3 ANSI Bins higher than the traditional LED used to create the combined light. For example, a traditional white LED with emission in the 4000 K ANSI Bin can be combined with a supplemental LED containing melanopic light (e.g., with spectrum 220 in FIG. 2A), and the spectrum of the combined light will have a higher melanopic light intensity than a traditional white LED with a 5700 K CCT or a 6500 K CCT. FIG. 2C shows that the two LEDs in this example can be combined to give a light that would be perceived as white (e.g., has chromaticity coordinates within the ANSI 4000 K Bin, or the ANSI 3500 K Bin) when using the 10-degree observer. However, the same two LEDs can only have a spectrum that appears white if a small amount of the supplemental LED is added to the traditional white light LED (i.e., has chromaticity coordinates within the ANSI 3500 K Bin) when using the 2-degree observer. As more supplemental LED light is added to the traditional white light LED using the 2-degree observer, then the chromaticity coordinates of the combined spectrum falls well below the black body locus and outside of the white light coordinate ranges (e.g., the ANSI 4000 K Bin, or the ANSI 3500 K Bin).

FIG. 2C also shows that these example LEDs can be combined such that the chromaticity coordinates of the combined spectrum are approximately within a 1-step MacAdam ellipse of the intersection of the 4000 K CCT line and the black body locus, in the 10-degree observer. In other embodiments, the light from a supplemental LED (e.g., with a melanopic emission spectrum) can be combined with the light from a second LED (e.g., a white light LED) and the chromaticity coordinates of the combined spectrum are approximately within a 1-step MacAdam ellipse of the intersection of the 3000 K CCT line, or the 3500 K CCT line and the black body locus, in the 10-degree observer. In some embodiments, the light from a supplemental LED (e.g., with a melanopic emission spectrum) can be combined with the light from a second LED (e.g., a white light LED) and the chromaticity coordinates of the combined spectrum are approximately within a 1-step MacAdam ellipse of the black body locus in the range of chromaticity coordinate x from 0.34 to 0.45.

In some embodiments, the emissions from an LED with a melanopic emission spectrum can be combined with that of a white light LED to produce a combined spectrum, and the chromaticity coordinates of the combine spectrum can lie within the region of the 10-degree observer in the CIE 1931 color space diagram bounded by the four (x,y) coordinates (0.367, 0.358), (0.373, 0.387), (0.390, 0.372), (0.401, 0.404), or bounded by the four (x,y) coordinates (0.389, 0.370), (0.399, 0.402), (0.415, 0.382), (0.430, 0.415), or bounded by the four (x,y) coordinates (0.415, 0.382), (0.437, 0.389), (0.430, 0.416), (0.456, 0.426), or bounded by the four (x,y) coordinates (0.437, 0.389), (0.456, 0.426), (0.481, 0.432), (0.459, 0.394), or bounded by the five (x,y) coordinates (0.34, 0.34), (0.46, 0.39), (0.48, 0.43), (0.38, 0.40), and (0.34, 0.36).

The example supplemental LED in FIGS. 2A-2C has chromaticity coordinates substantially below the black body locus, which would make it an improper match with a traditional white light, using the industry standard 2-degree observer. Surprisingly however, in the 10-degree observer, the chromaticity coordinates of the supplemental LED lie above the black body locus. The 10-degree color blend line in FIG. 2C shows that the supplemental LED in FIGS. 2A-2C can be combined with a 3500 K white light to create 4000 K white light within approximately a one-step MacAdam ellipse using the 10-degree observer. In other embodiments, the same supplemental LED could be combined with a 3000 K white light to create a 3500 K white light within a one-step MacAdam ellipse using the 10-degree observer.

Figure 2D:
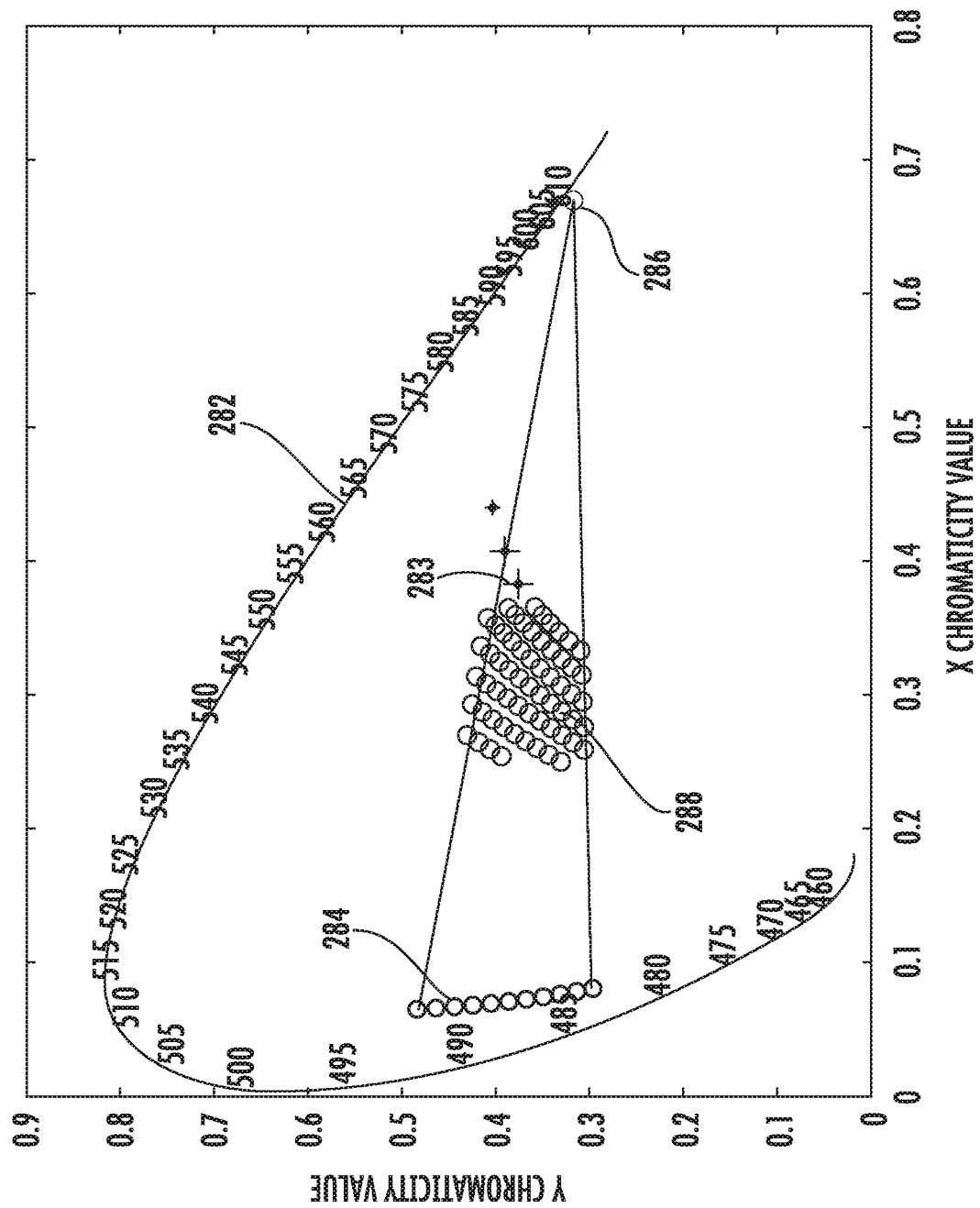
FIG. 2D shows additional examples of chromaticity coordinates of supplemental LEDs with a primary light source and a phosphor, in accordance with some embodiments.
Figure 2E:
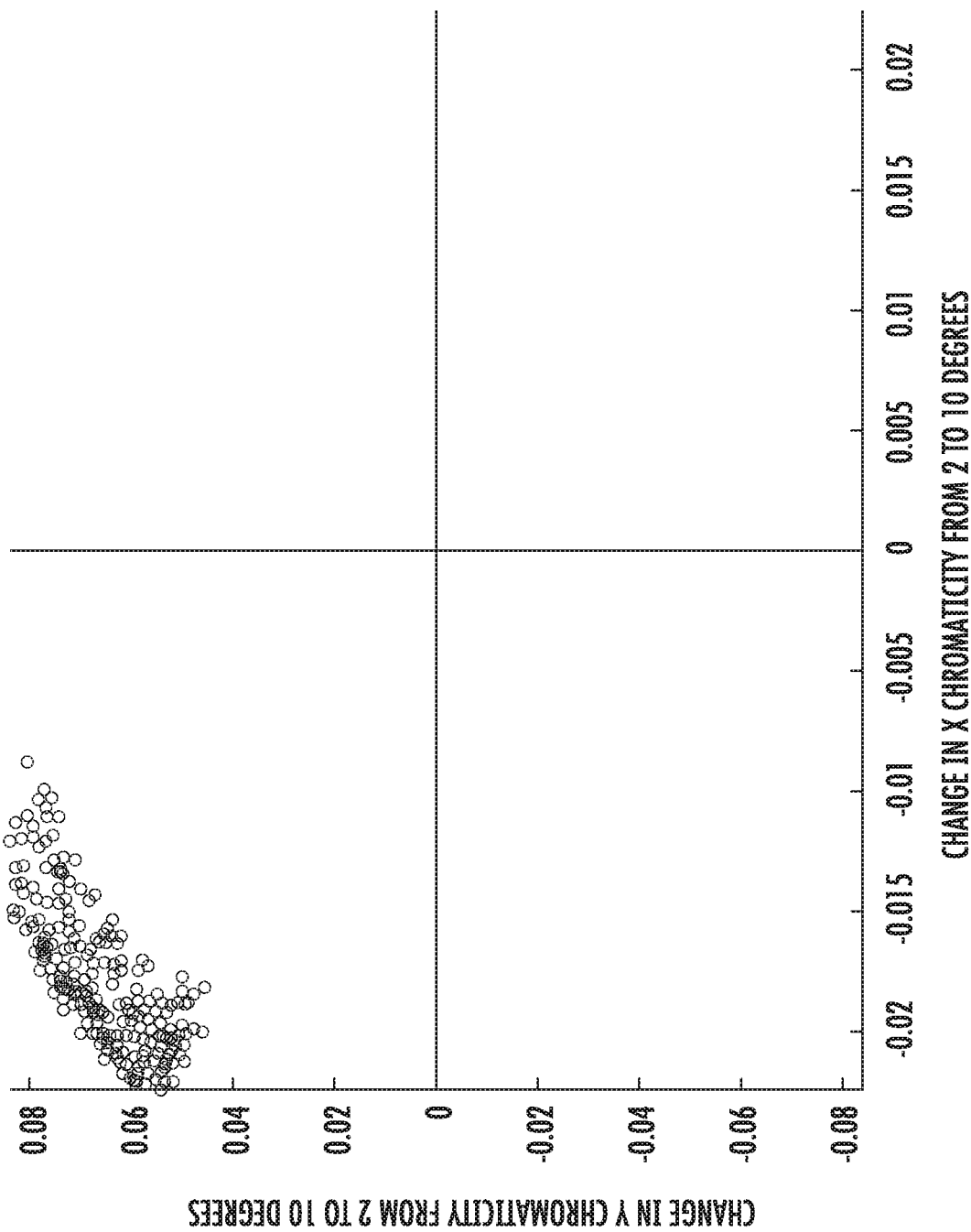
FIG. 2E shows example shifts in chromaticity coordinates from the 2-degree to the 10-degree observers for the supplemental LEDs in FIG. 2D, in accordance with some embodiments.
Figure 2F:
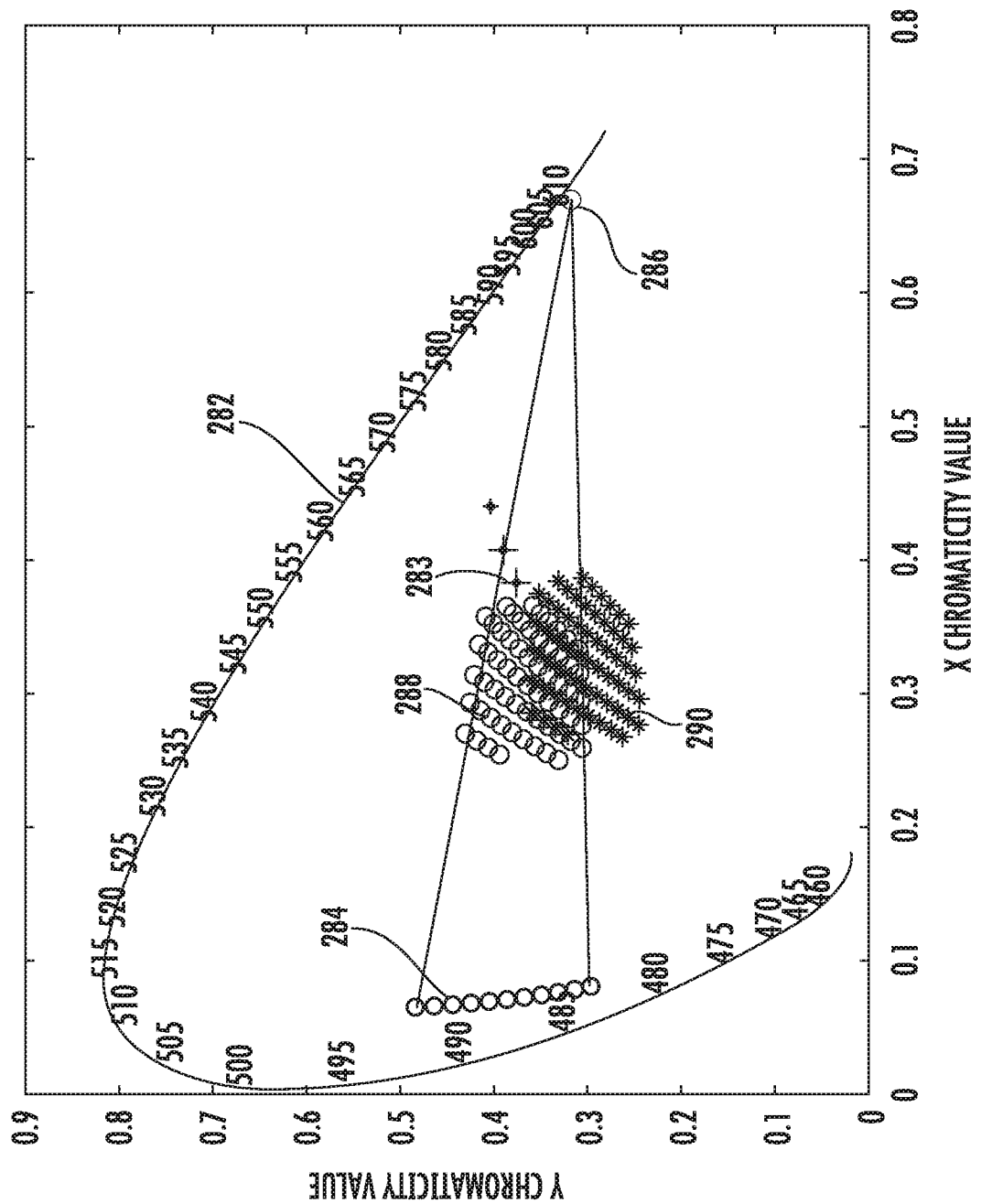
FIG. 2F shows examples of chromaticity coordinates resulting from mixing a primary light source and a phosphor for supplemental LEDs using the 2-degree observer, in accordance with some embodiments.

The example supplemental LED shown in FIGS. 2A-2C is only one example of a supplemental LED light that can be combined with a common white LED light to create an acceptable white light with a large amount of energy in the melanopic wavelength region (i.e., with a melanopic emission spectrum). Some additional examples of chromaticity coordinates of supplemental LEDs with a primary light source and a phosphor are shown in FIG. 2D, which use the 10-degree observer. In the example shown in FIG. 2D, a supplemental LED has a primary light source emitting light having chromaticity coordinates 284, and a phosphor emitting light having chromaticity coordinates 286. In some embodiments, the combined light from the primary light source and the phosphor will have chromaticity coordinates 288. The curve 282 shows the chromaticity coordinates for the wavelengths labeled on the curve, using the 10-degree observer. The crosses in the figure near chromaticity coordinate (0.4, 0.4) are points on the blackbody locus, for example point 283 has a CCTs of about 4000 K. Similar to the example shown in FIG. 2B, the chromaticity coordinates 288 of the supplemental LEDs in FIG. 2D will each have a large vector magnitude shift in the negative x, positive y direction between the 2-degree and the 10-degree observer. FIG. 2E plots the shift in chromaticity coordinates from the 2-degree to the 10-degree observers for the supplemental LEDs in FIG. 2D, and shows that the shifts have magnitudes greater than 0.04. FIG. 2F shows chromaticity coordinates 290, which result from mixing the primary light source and the phosphor for the supplemental LEDs in this example using the 2-degree observer. In some embodiments, the primary light source and/or the phosphor in the supplemental LED are chosen such that the chromaticity coordinates of the supplemental LED have certain values, and then the supplemental LED is combined with a traditional white light LED such that the combined light appears white. In some cases, different supplemental LEDs will be designed to be compatible with different white light sources, such that the combined light appears white. Varying the color (or chromaticity coordinates) of the primary light source and/or the phosphor of the supplemental LED provides an extra degree of freedom when combining a supplemental LED with a traditional white light LED. This extra degree of freedom can enable the combined color of the supplemental LED (with a melanopic emission spectrum) and the traditional white light LED to appear white (i.e., to an average human).

Figure 3A:
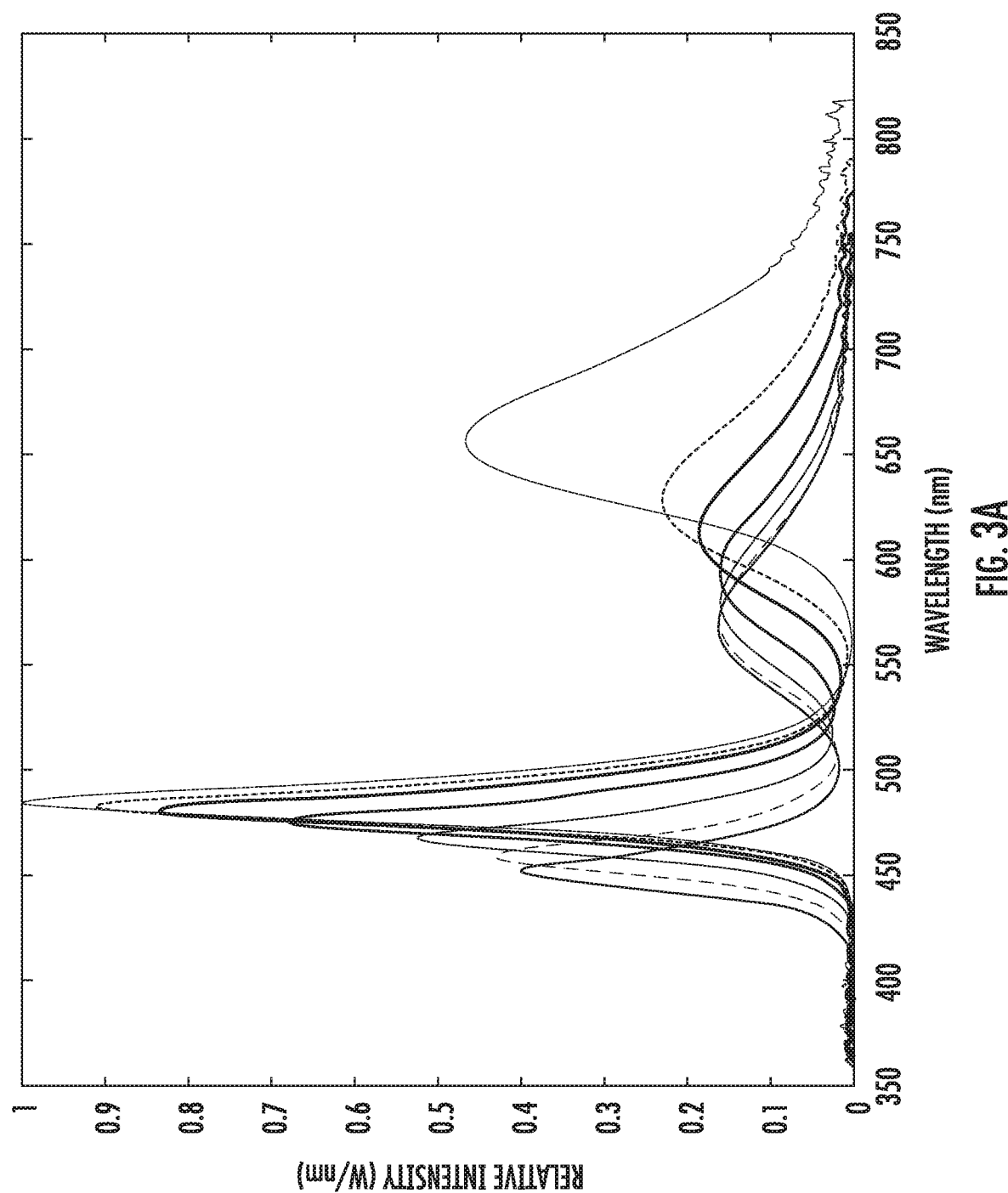
FIG. 3A shows examples of different spectra with various amounts of light intensity in the melanopic wavelength range, in accordance with some embodiments.
Figure 3B:
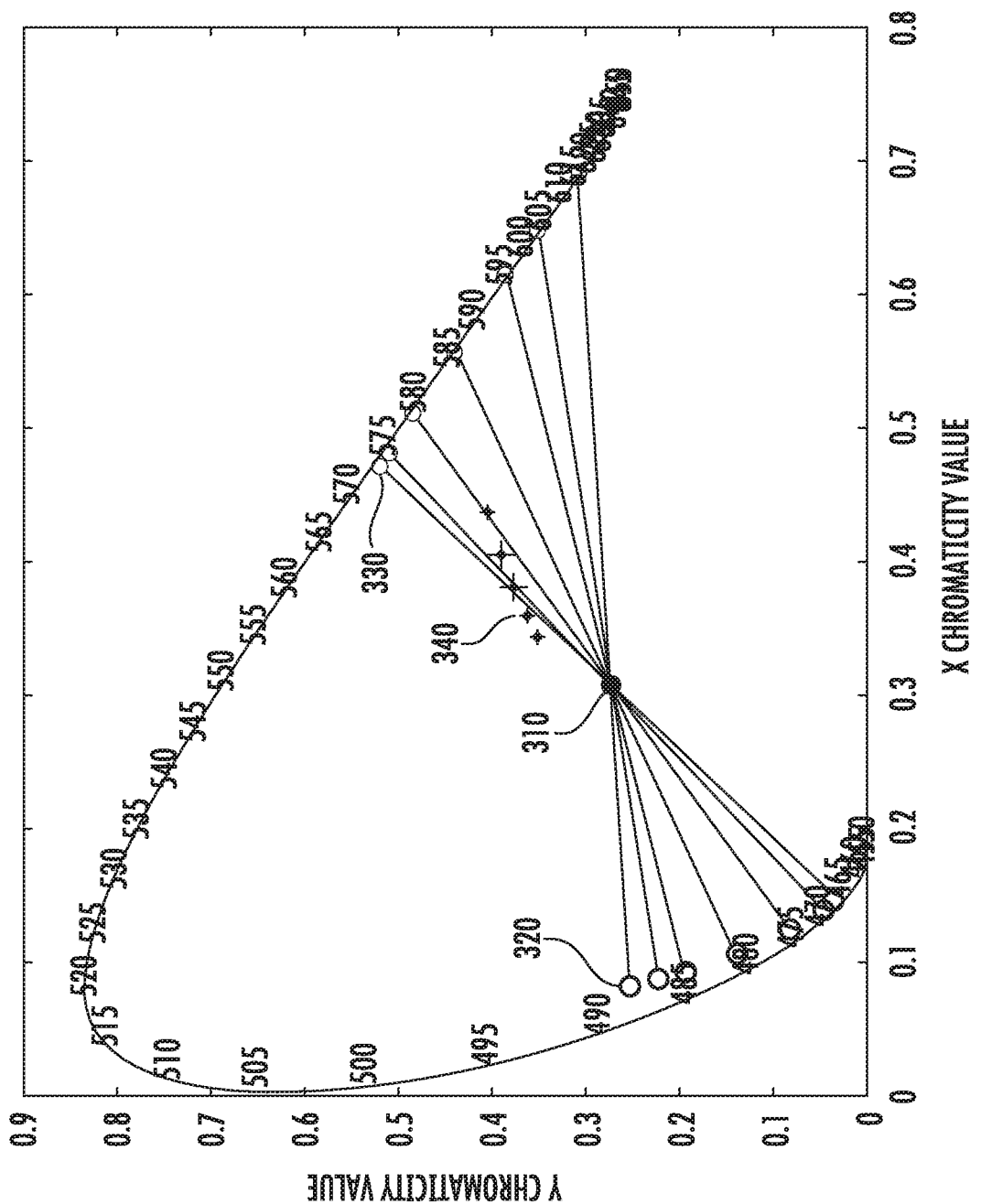
FIG. 3B shows the chromaticity coordinates for the example spectra shown in FIG. 3A, in accordance with some embodiments.

Additionally, different spectra can be designed to achieve given chromaticity coordinates. FIG. 3A shows a series of different spectra with various amounts of light intensity in the melanopic wavelength range. The spectra in FIG. 3A each have a strong peak in a wavelength region from approximately 460 nm to 490 nm, and a weaker peak in the wavelength range from approximately 570 nm to 610 nm. FIG. 3B shows that each of the spectra shown in FIG. 3A have approximately the same chromaticity coordinates 310 (i.e., at approximately x=0.32, y=0.27). FIG. 3B also shows how this is accomplished, since the color mixing lines between the chromaticity coordinates 320 of the strong peak and the chromaticity coordinates 330 of the weak peak for each spectrum cross at a single point 310. The crosses 340 are points on the blackbody locus with different CCTs.

Figure 3C:
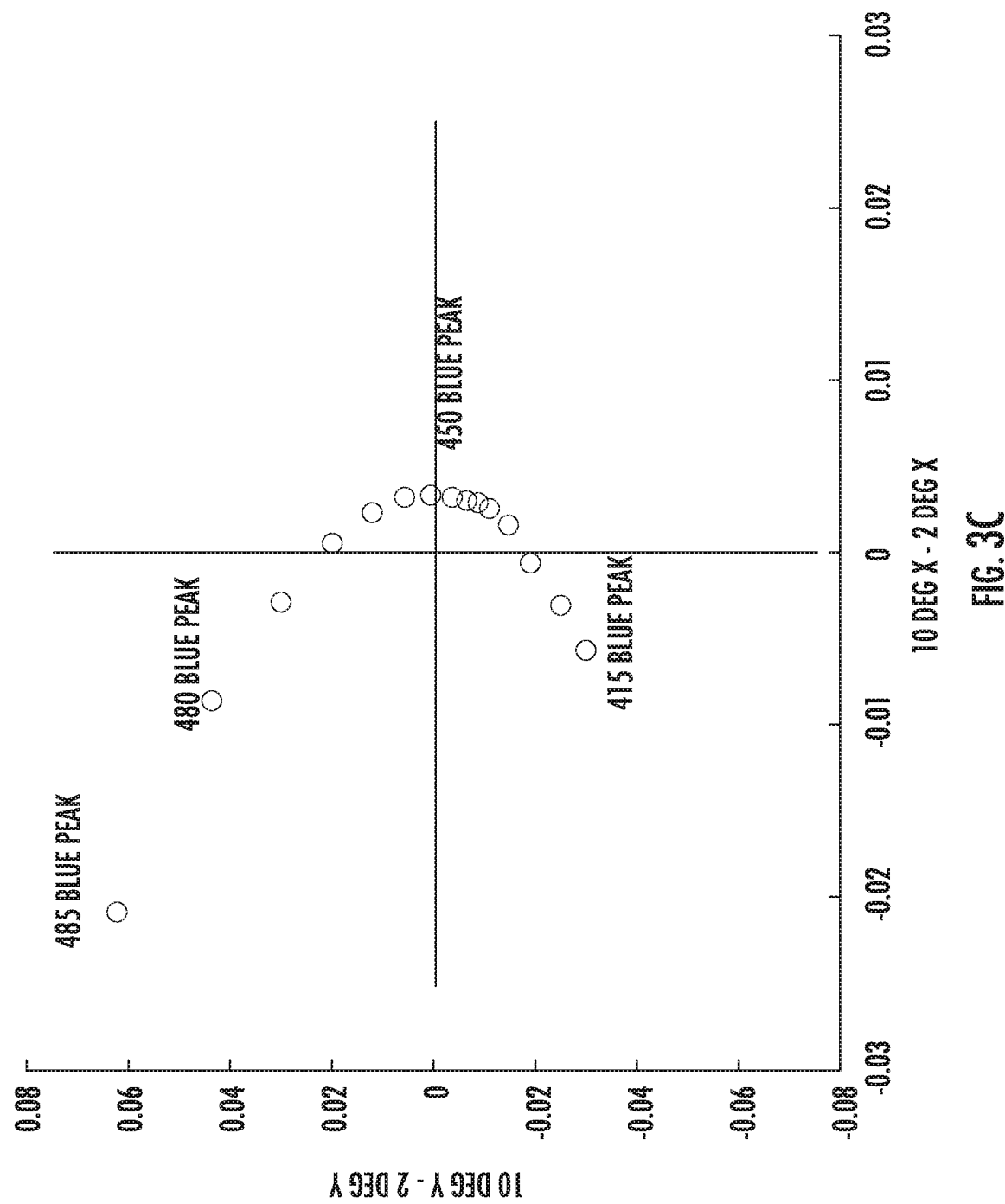
FIG. 3C shows the shift in chromaticity coordinates from the 2-degree observer to the 10-degree observer for the example spectra shown in FIG. 3A, in accordance with some embodiments.

Surprisingly, the chromaticity shift from the 2-degree to the 10-degree observer is significantly different for the different spectra shown in FIG. 3A. FIG. 3C shows the shift in chromaticity coordinates from the 2-degree observer to the 10-degree observer for the spectra shown in FIG. 3A. The spectrum with the strong peak (i.e., the "blue peak") at approximately 485 nm has a large positive change in the y-direction and a large negative change in the x-direction. In contrast, the spectrum with the strong peak (i.e., the "blue peak") at approximately 450 nm has almost no change in the y-direction and a small positive change in the x-direction. In contrast, the spectrum with the strong peak (i.e., the "blue peak") at approximately 415 nm has a moderate negative change in the y-direction and a moderate negative change in the x-direction. This example illustrates that spectra with high melanopic light intensities (i.e., in the 480 nm to 500 nm wavelength range) can have large shifts in the chromaticity coordinates, and in opposite directions, compared with other spectra without high melanopic light intensities.

In some embodiments, a supplemental LED emitting melanopic light can be combined with one or more white LEDs of various CCTs, such that the combined illumination from the set of LEDs has certain chromaticity coordinates, and a CRI, COI, and/or melanopic lux equivalent (MLE), tuned or optimized to various values. MLE is a measure of the flux density of light in a given spectrum weighted by the luminous efficiency function 120 in FIG. 1, which is based on the action spectrum of melanopsin photoreceptors (and the spectrum is not weighted by the photopic luminous efficiency function based on the response of foveal cones). Additionally, the wall-plug efficiency (WPE) of the set of LEDs can be tuned or optimized along with the spectral properties.

The supplemental LEDs can be combined with multiple options for white points to create a system which can be tuned for high visual efficacy or high biological efficacy, or can modulate back and forth between different setpoints. For example, the supplemental LED can be combined with one of many different CCT white light LEDs and still arrive at a color point of 4000 K. However, the amount of melanopic light may be different, even though the color point is the same. For example, if a supplemental LED is combined with an LED with a CCT closer to 4000 K (3900 K for example), then less of the supplemental LED may be required to achieve the end target of 4000 K, and conversely, if a supplemental LED is combined with an LED with a CCT farther from the end target (3200 K for example) then more of the supplemental LED may be required to achieve the end target of 4000 K. The amount of melanopic light needed to match a particular color will depend on the spectrum of the supplemental LED (which may not be focused on maximizing visual efficiency, but rather may be focused on the biological efficiency) and the white LED. In some cases, there is a tradeoff between high visual efficacy and high biological efficacy, as shown in the examples below.

Figure 4A:
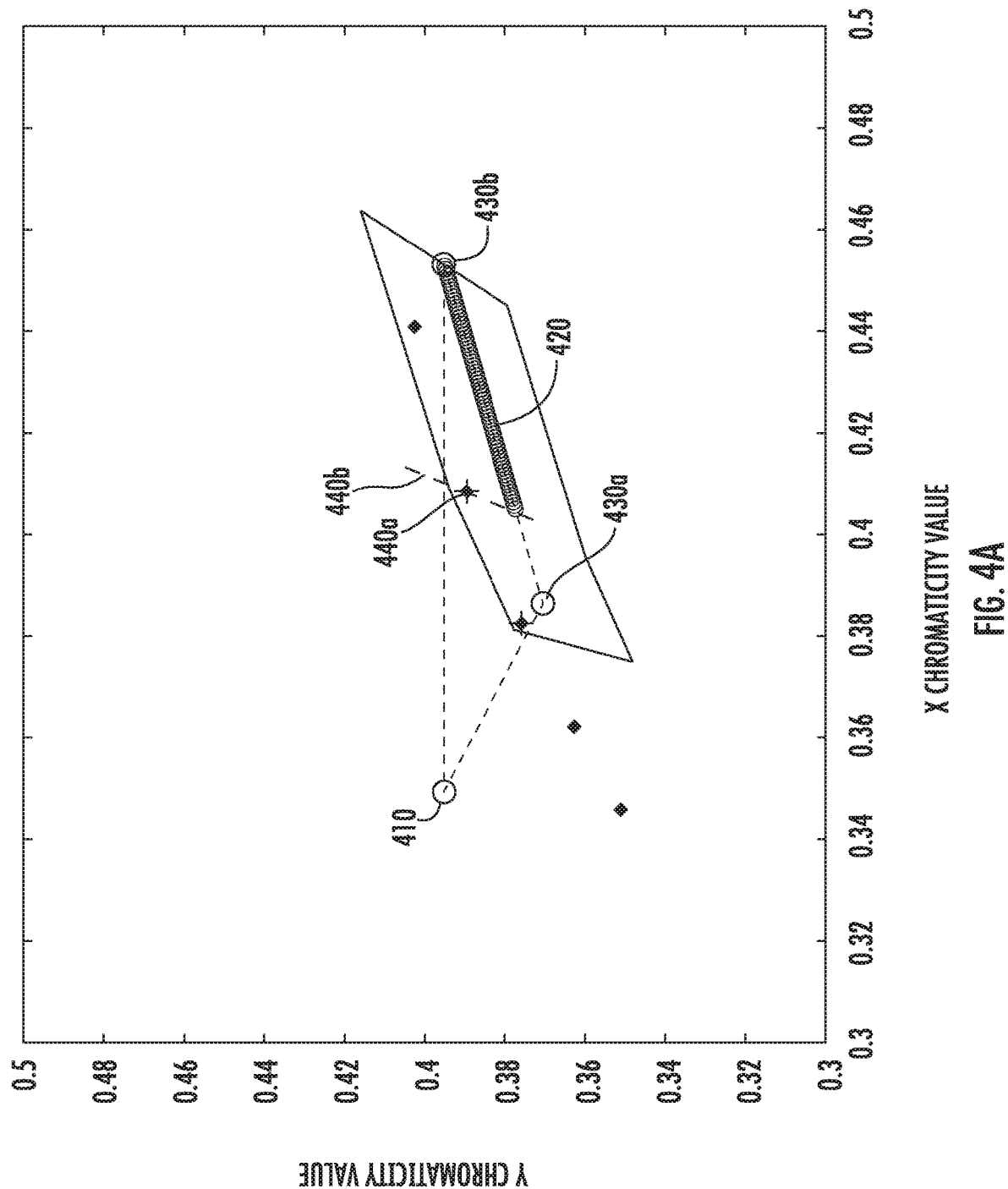
FIG. 4A shows a section of the 1931 CIE color space diagram with an example supplemental LED and an example set of white LEDs, in accordance with some embodiments.
Figure 4B:
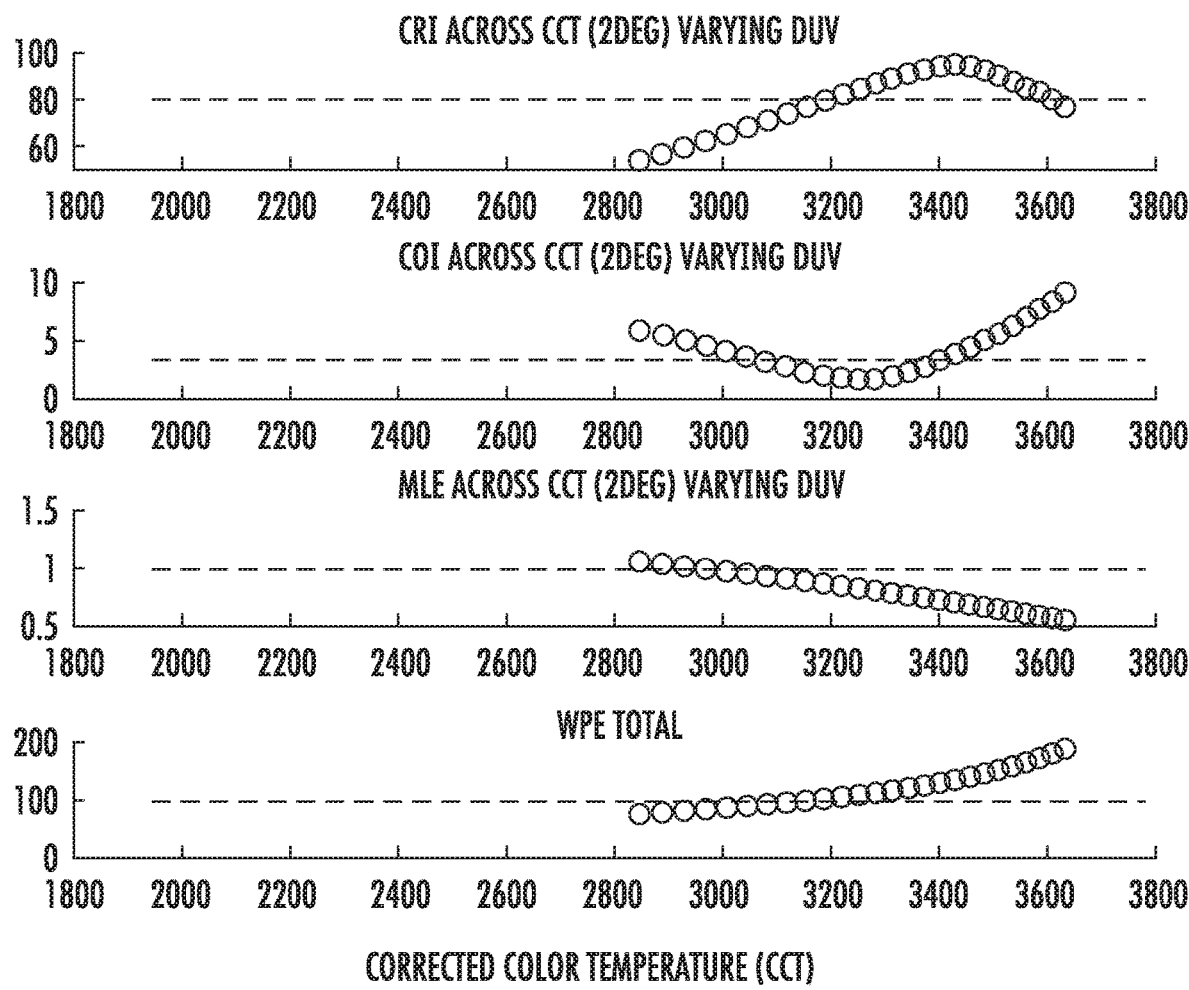
FIG. 4B shows example metrics of the combined illumination from the example supplemental LED and an example set of white LEDs in FIG. 4A, in accordance with some embodiments.
Figure 5B:
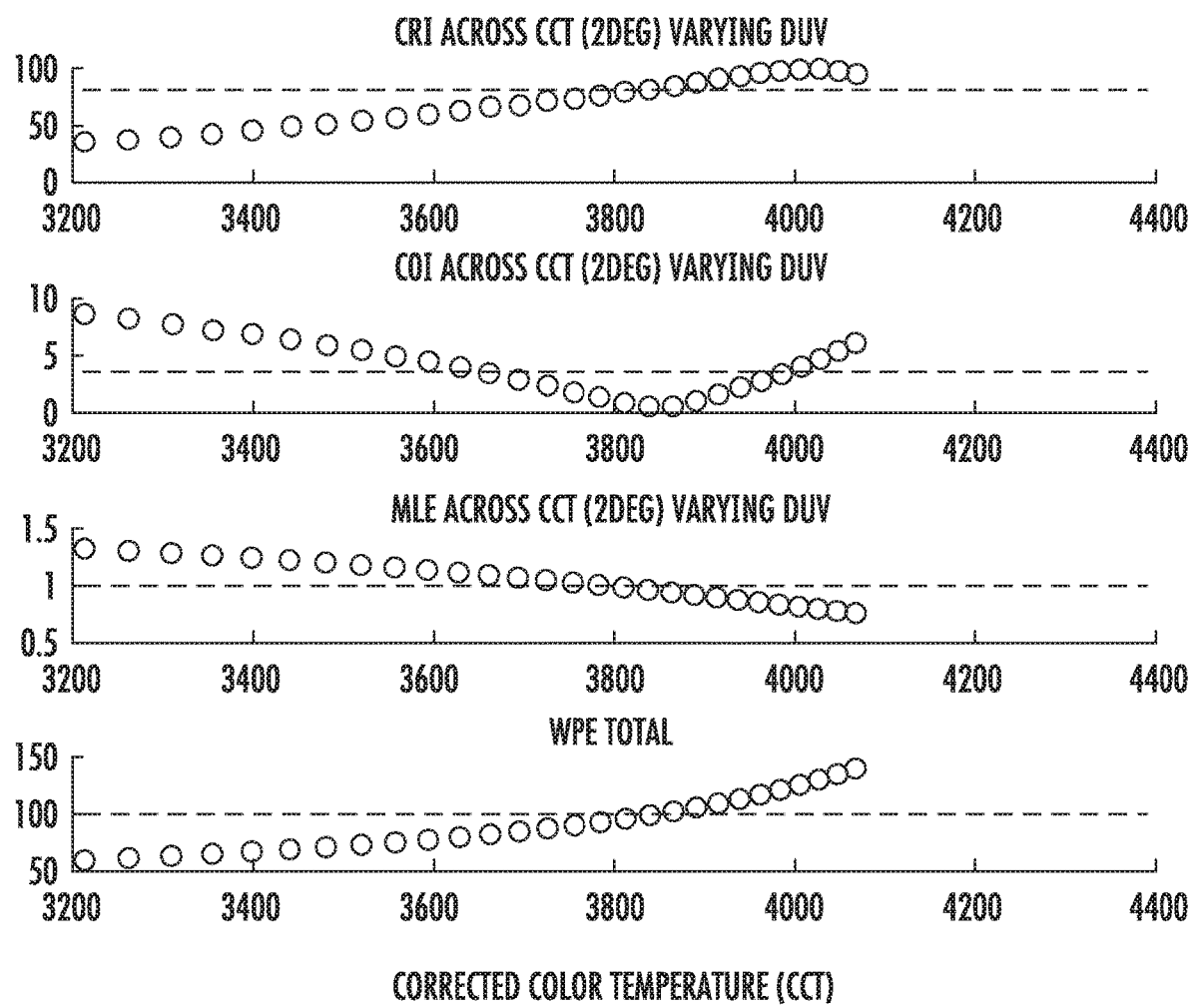
FIG. 5B shows example metrics of the combined illumination from the example supplemental LED and an example set of white LEDs in FIG. 5A, in accordance with some embodiments.

FIGS. 4A-4B and 5A-5B show non-limiting examples of a supplemental LED emitting melanopic light combined with various white LEDs, such that the combined light from the set of LEDs has chromaticity values with a 3500 K target (FIGS. 4A-4B) or a 4000 K target (FIGS. 5A-5B). The examples in FIGS. 4A-5B are non-limiting examples only, and the supplemental LED may have different chromaticity coordinates than the example shown.

FIG. 4A shows a section of the 1931 CIE color space diagram with the supplemental LED 410 and a set of white LEDs 420. The white LEDs lie along a line between the points 430a (about 2700 K white light) and 430b (about 3600 K white light). In this first example, point 440a is the target color for the combined illumination from LED 410 and a second LED chosen from the set of LEDs 420, and is within the ANSI 3500 K Bin. Line 440b shows a possible set of color points within the ANSI 3500 K Bin that are achievable by mixing the LED 410 with a second LED chosen from the set of LEDs 420.

FIG. 4B shows various metrics of the combined illumination from LED 410 and a second LED chosen from the set of LEDs 420 in FIG. 4A. The x-axes of the four plots in FIG. 4B are the CCT of the LED 420 that is mixed with the LED 410. The y-axes all relate to the total combined spectrum from 410 and 420, and are, from the top plot to the bottom plot in the figure, CRI, COI, MLE, all in the 2-degree observer, and the WPE for LEDs 410 and 420 together. In this example, maximizing MLE entails mixing the LED 410 with an LED 420 with a low CCT (e.g., near 2850 K). However, the CRI has a maximum value when the LED 420 has a CCT of about 3450 K. Furthermore, COI has a minimum value (lower COI is better) when the LED 420 has a CCT of about 3250 K. And, the WPE is maximized by mixing the LED 410 with an LED 420 that has a high CCT (e.g., near 3650 K).

FIG. 5A shows a section of the 1931 CIE color space diagram with the supplemental LED 410 and a set of white LEDs 520. The white LEDs lie along a line between the points 430a (about 2700 K white light) and 430b (about 3600 K white light). In this second example, point 540a is the target color for the combined illumination from LED 410 and a second LED chosen from the set of LEDs 520, and is within the ANSI 4000 K Bin. Line 540b shows a possible set of color points within the ANSI 4000 K Bin that are achievable by mixing the LED 410 with a second LED chosen from the set of LEDs 520.

FIG. 5B shows various metrics of the combined illumination from LED 410 and a second LED chosen from the set of LEDs 520 in FIG. 5A. The x-axes and y-axes of the four plots in FIG. 5B are the same as in FIG. 4B. In this example, maximizing MLE entails mixing the LED 410 with an LED 520 with a low CCT (e.g., near 3200 K). However, the CRI has a maximum value when the LED 420 has a CCT of about 4050 K. Furthermore, COI has a minimum value (lower COI is better) when the LED 420 has a CCT of about 3850 K. And, the WPE is maximized by mixing the LED 410 with an LED 520 that has a high CCT (e.g., near 4050 K).

FIGS. 4A-5B show two examples for 3500 K and 4000 K target colors that illustrate that different metrics can vary based on the CCT of the white light LED combined with a supplemental LED containing melanopic light. In some cases, the MLE increases as the CCT of the white light LED decreases. In some cases, the WPE increases as the CCT of the white light LED increases. In some cases, the CRI has a maximum when the CCT of the second LED is from about 3200 K to about 4200 K, or from about 3600 K to about 4000 K. In some cases, the COI has a minimum when the CCT of the second LED is from about 3000 K to about 4200 K, or from about 3200 K to about 4000 K.

In some embodiments, a supplemental LED and a white light LED can be mixed and the CRI of the spectrum, COI of the spectrum, MLE of the spectrum, and/or the WPE of the LEDs can be optimized according to any criteria or optimization function. The trends observed in the 10-degree observer are similar to those shown in FIGS. 4B and 5B (using the 2-degree observer), and therefore all of the same systems and methods regarding mixing the light output from a supplemental LED and a white light LED to optimize the CRI of the spectrum, COI of the spectrum, MLE of the spectrum, and/or the WPE described herein can be performed using the 2-degree observer or the 10-degree observer. Some non-limiting example criteria and/or optimization functions are as follows.

An example of an optimization function includes a minimum value for one metric and the maximization of another. For example, the white light LED CCT can be chosen such that the combined light has a CRI greater than 80, and a maximum MLE. In the case of a 4000 K target color, these criteria would lead to the choice of a white light LED with a CCT of about 3800 K. In that case, the CRI would be about 80, and the MLE would be about 1. 3800 K is the optimal white light LED CCT in this case because combinations with higher CCT white LEDs would have lower MLE, and combinations with lower CCT white LEDs would have CRIs less than 80.

In another example, the CRI, COI, MLE and WPE can all be assigned weights and then combined in a linear combination in a function resulting in an aggregate score, and that aggregate score can be maximized (or minimized). For example, such a function can take the form:

$$A*CRI+B*COI+C*MLE+D*WPE=X \qquad \text{(Equation 1)}$$

where, A, B, C and D are the weighting factors for the values of CRI, COI, MLE and WPE (e.g., as shown in FIGS. 4B and 5B), and X is the aggregate score that can be maximized (or minimized, in some cases). In some embodiments, the weighting factors A, B, C and D can have values from 0 to 1.

In other examples, the optimization function used to combine the values of CRI, COI, MLE and WPE into an aggregate score to be optimized may be nonlinear, and in some cases may include nonlinear interactions (i.e., cross-products) of the CRI, COI, MLE and WPE values.

In some cases, the optimization function can be a power series. For example, such a function can take the form:

$$A*(CRI)^i+B*(COI)^j+C*(MLE)^k+D*(WPE)^l=X \qquad \text{(Equation 2)}$$

where, A, B, C and D are coefficients for the values of CRI, COI, MLE and WPE (e.g., as shown in FIGS. 4B and 5B), i, j, k, and l are exponents (which can be positive or negative numbers), and X is the aggregate score that can be maximized (or minimized, in some cases). In some embodiments, the coefficients A, B, C and D can have values from 0 to 1, and the exponents i, j, k and l can have vales from −10 to 10, or 1 to 10, or −10 to −1. This type of function is useful when some of the parameters should be maximized (e.g., higher MLE is better) and some should be minimized (e.g., lower COI is better). By making some of the exponents negative, and some positive, all of the parameters can be optimized together, even though some should be minimized and some should be maximized. In other embodiments, more terms can also be included in a power series optimization equation, such as nonlinear interactions (i.e., cross-products) of the CRI, COI, MLE and WPE values, with or without higher order exponents as well.

Figure 6A:
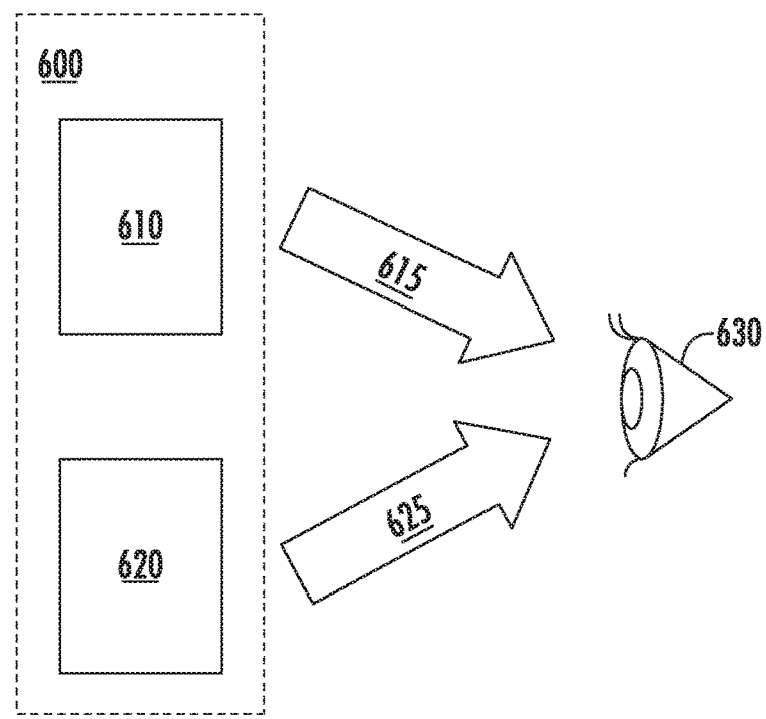
FIG. 6A shows an example of a light emitting apparatus containing a supplemental LED and a white LED, in accordance with some embodiments.
Figure 6B:
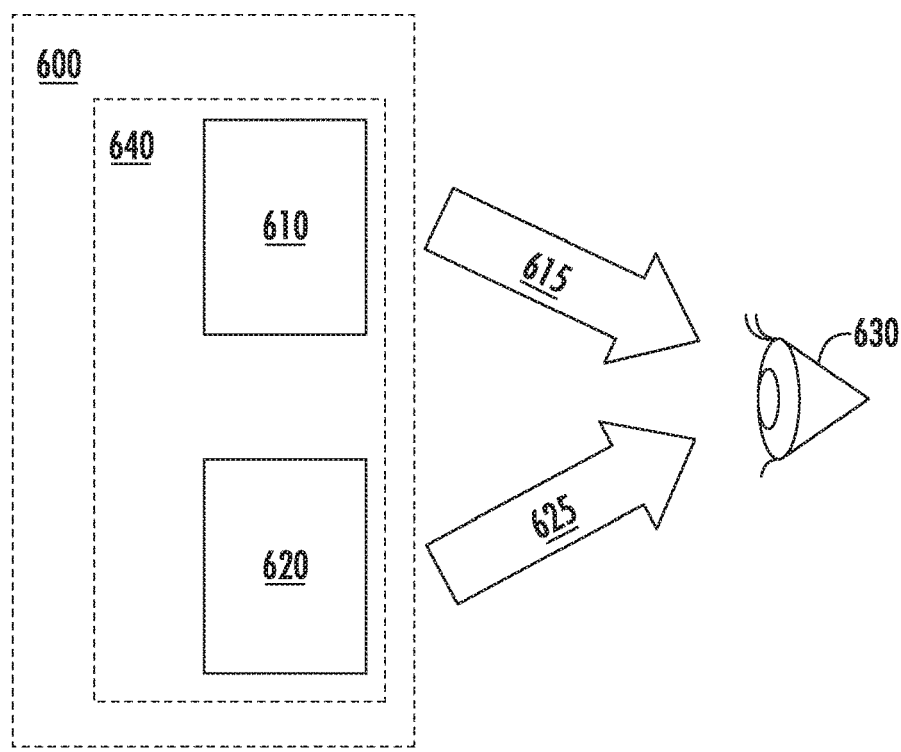
FIG. 6B shows an example of a light emitting apparatus containing a supplemental LED and a white LED that are contained within a single unit, in accordance with some embodiments.
Figure 6C:
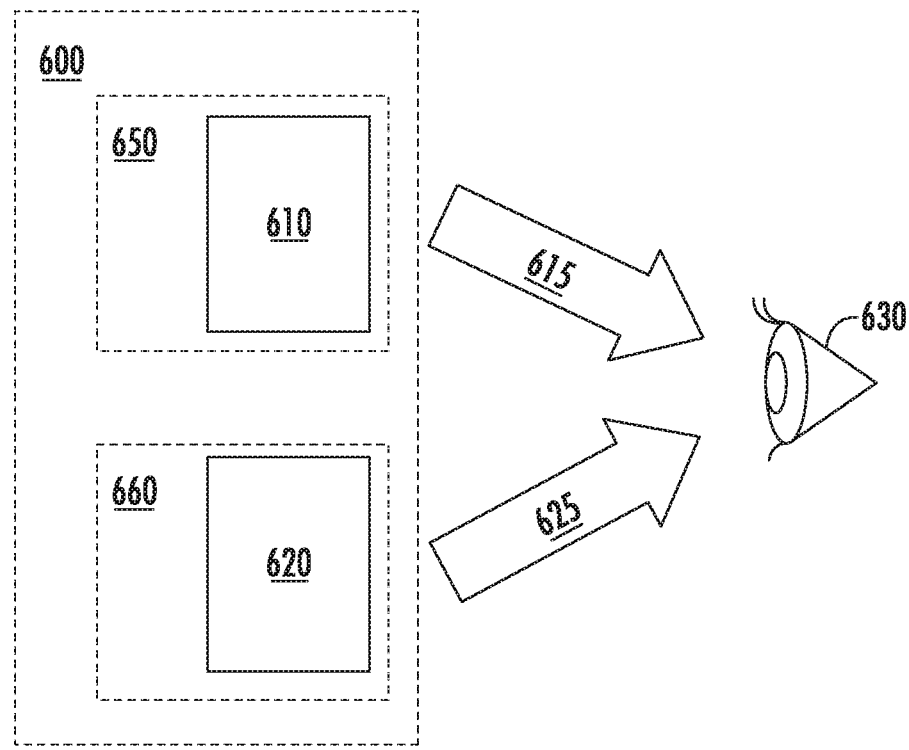
FIG. 6C shows an example of a light emitting apparatus containing a supplemental LED and a white LED that are contained in two separate units, in accordance with some embodiments.

The LEDs within the light emitting apparatuses described herein can be physically configured in different ways. FIG. 6A shows an example of a light emitting apparatus 600 containing a supplemental LED 610 and a white LED 620, and the light 615 and 625 from the two LEDs 610 and 620 respectively combine to produce white light emitted from the apparatus that appears white to an average observer 630, in accordance with some embodiments. FIGS. 6B and 6C show examples where the 2 LEDs are configured in different types of light emitting apparatuses 600, where the light 615 and 615 from the two LEDs 610 and 620 respectively combine to produce white light emitted from the apparatus that appears white to an average observer 630. FIG. 6B shows an example of a light emitting apparatus 600 containing a supplemental LED 610 and a white LED that are contained within a single unit 640, where this unit 640 is a housing, chassis, or enclosure, and/or are connected to the same fixture. For example, a single lighting unit can contain both LEDs, in accordance with some embodiments. FIG. 6C shows an example of a light emitting apparatus 600 containing a supplemental LED 610 and a white LED 620 that are contained in two separate units 650 and 660, and are not contained within a single housing, chassis, or enclosure, and/or are not connected to the same lighting fixture, in accordance with some embodiments. For example, the white LED 620 can be contained in a first fixture 650, and the supplemental LED 610 can be contained in a physically separated lighting fixture 660. In some embodiments, the supplemental and white LEDs are controlled and/or driven by the same electronic system and/or power supply (not shown), while in other embodiments, the supplemental and white LEDs are controlled and/or driven by different electronic systems and/or power supplies (not shown).

Reference has been made in detail to embodiments of the disclosed invention, one or more examples of which have been illustrated in the accompanying figures. Each example has been provided by way of explanation of the present technology, not as a limitation of the present technology. In fact, while the specification has been described in detail with respect to specific embodiments of the invention, it will be appreciated that those skilled in the art, upon attaining an understanding of the foregoing, may readily conceive of alterations to, variations of, and equivalents to these embodiments. For instance, features illustrated or described as part of one embodiment may be used with another embodiment to yield a still further embodiment. Thus, it is intended that the present subject matter covers all such modifications and variations within the scope of the appended claims and their equivalents. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only, and is not intended to limit the invention.

What is claimed is:

1. A light emitting apparatus, comprising:
a first light emitting diode (LED) with an emission spectrum comprising a corrected color temperature from 3000 K to 4000 K; and
a second LED with a melanopic emission spectrum comprising:
a first peak centered at a wavelength from 480 nm to 500 nm; and
a second peak centered at a wavelength from 640 nm to 750 nm;
wherein the intensity of the first peak is greater than the intensity of the second peak;
wherein:
light is emitted from the light emitting apparatus comprising light from the first and second LEDs, and the emitted light comprises:
chromaticity coordinates (x,y), in the CIE 1931 color space diagram using the 1964 10° Supplementary Standard Observer, that are within a one-step MacAdam ellipse from the black body locus in the range of chromaticity coordinate x from 0.34 to 0.45;
a cyanosis observation index (COI) less than 3.3; and
a color rendering index (CRI) greater than 80.

2. The light emitting apparatus of claim 1, wherein:
the light emitted from the light emitting apparatus comprising light from the first and second LEDs, and the emitted light comprises chromaticity coordinates (x,y), in the CIE 1931 color space diagram using the 1964 10° Supplementary Standard Observer, that are within a region bounded by the four (x,y) coordinates (0.367, 0.358), (0.373, 0.387), (0.390, 0.372), (0.401, 0.404).

3. The light emitting apparatus of claim 1, wherein:
the light emitted from the light emitting apparatus comprising light from the first and second LEDs, and the emitted light comprises chromaticity coordinates (x,y), in the CIE 1931 color space diagram using the 1964 10° Supplementary Standard Observer, that are within a region bounded by the four (x,y) coordinates (0.389, 0.370), (0.399, 0.402), (0.415, 0.382), (0.430, 0.415).

4. The light emitting apparatus of claim 1, wherein:
the light emitted from the light emitting apparatus comprising light from the first and second LEDs, and the emitted light comprises chromaticity coordinates (x,y), in the CIE 1931 color space diagram using the 1964 10° Supplementary Standard Observer, that are within a region bounded by the four (x,y) coordinates (0.415, 0.382), (0.437, 0.389), (0.430, 0.416), (0.456, 0.426).

5. The light emitting apparatus of claim 1, wherein:
the light emitted from the light emitting apparatus comprising light from the first and second LEDs, and the emitted light comprises chromaticity coordinates (x,y), in the CIE 1931 color space diagram using the 1964 10° Supplementary Standard Observer, that are within a region bounded by the four (x,y) coordinates (0.437, 0.389), (0.456, 0.426), (0.481, 0.432), (0.459, 0.394).

6. The light emitting apparatus of claim 1, wherein:
chromaticity coordinates (x,y) of the first light emitting diode (LED), in the CIE 1931 color space diagram using the 1964 10° Supplementary Standard Observer, comprise x from 0.40 to 0.42, and y from 0.38 to 0.40; and
chromaticity coordinates (x,y) of the second LED, in the CIE 1931 color space diagram using the 1964 10° Supplementary Standard Observer, comprise x from 0.22 to 0.43, and y from 0.34 to 0.47.

7. The light emitting apparatus of claim 1, wherein:
chromaticity coordinates (x,y) of the first light emitting diode (LED), in the CIE 1931 color space diagram using the 1964 10° Supplementary Standard Observer, are within the ANSI 3500 K Bin; and
chromaticity coordinates (x,y) of the second LED, in the CIE 1931 color space diagram using the 1964 10° Supplementary Standard Observer, comprise x from 0.22 to 0.43, and y from 0.34 to 0.47.

8. The light emitting apparatus of claim 1, wherein:

chromaticity coordinates (x,y) of the first light emitting diode (LED), in the CIE 1931 color space diagram using the 1931 2° Standard Observer, are within the ANSI 3500 K Bin; and chromaticity coordinates (x,y) of the second LED, in the CIE 1931 color space diagram using the 1931 2° Standard Observer, comprise x from 0.23 to 0.45, and y from 0.28 to 0.39.

9. The light emitting apparatus of claim 1, wherein:

the second light emitting diode (LED) comprises a primary light source and a phosphor, and wherein:

the primary light source has an emission spectrum comprising a peak centered at a wavelength from 480 nm to 500 nm; and the phosphor has an emission spectrum, when excited by the light from the primary light source, comprising a peak centered at a wavelength from 640 nm to 750 nm.

10. The light emitting apparatus of claim 1, wherein:

the second light emitting diode (LED) comprises a primary light source and a phosphor, and wherein:

chromaticity coordinates (x,y) of the emission spectrum from the primary light source in the second LED, in the CIE 1931 color space diagram using the 1964 10° Supplementary Standard Observer, comprise x from 0.06 to 0.08, and y from 0.36 to 0.53; and chromaticity coordinates (x,y) of the emission spectrum from the phosphor in the second LED, in the CIE 1931 color space diagram using the 1964 10° Supplementary Standard Observer, comprise x from 0.55 to 0.68, and y from 0.31 to 0.4.

11. The light emitting apparatus of claim 1, wherein:

chromaticity coordinates (x,y) of the second light emitting diode (LED), in the CIE 1931 color space diagram, shift in the negative x direction and the positive y direction from the chromaticity coordinates using the 1931 2° Standard Observer to the chromaticity coordinates using the 1964 10° Supplementary Standard Observer.

12. The light emitting apparatus of claim 11, wherein:

the shift in the chromaticity coordinates (x,y) of the second light emitting diode (LED) between the chromaticity coordinates using the 1931 2° Standard Observer and the chromaticity coordinates using the 1964 10° Supplementary Standard Observer, in the CIE 1931 color space diagram, comprise a shift in the x-coordinate from −0.025 to −0.01, and a shift in the y-coordinate from 0.04 to 0.09.

13. The light emitting apparatus of claim 11, wherein:

the shift in the chromaticity coordinates (x,y) of the second light emitting diode (LED) between the chromaticity coordinates using the 1931 2° Standard Observer and the chromaticity coordinates using the 1964 10° Supplementary Standard Observer, in the CIE 1931 color space diagram, has a magnitude greater than 0.04.

14. The light emitting apparatus of claim 1, wherein:

the chromaticity coordinates (x,y) of the second light emitting diode (LED), in the CIE 1931 color space diagram, are below the black body locus using the 1931 2° Standard Observer and above the black body locus using the 1964 10° Supplementary Standard Observer.

15. The light emitting apparatus of claim 1, wherein:

the spectrum of the light that is emitted from the light emitting apparatus comprising light from the first and second light emitting diodes (LEDs) further comprises a global maximum in power density at a wavelength from 480 nm to 500 nm.

16. The light emitting apparatus of claim 1, wherein:

the spectrum of the light that is emitted from the light emitting apparatus comprising light from the first and second light emitting diodes (LEDs) is strongly absorbed by melanopsin and satisfies proper circadian regulation in humans.

17. The light emitting apparatus of claim 1, wherein:

the light emitted from the light emitting apparatus comprises a first intensity of light from the first LED and a second intensity of light from the second LED; and a ratio of the first intensity to the second intensity is configured such that a color rendering index (CRI) of the light emitted from the light emitting apparatus is greater than 80 and the melanopic lux equivalent (MLE) is greater than 0.5.

* * * * *